(12) United States Patent
Zhou et al.

(10) Patent No.: US 12,023,167 B2
(45) Date of Patent: Jul. 2, 2024

(54) METHOD AND APPARATUS FOR IMPLANTATION OF A PACING ELECTRODE

(71) Applicant: Medtronic, Inc., Minneapolis, MN (US)

(72) Inventors: Xiaohong Zhou, Woodbury, MN (US); Wade M. Demmer, Coon Rapids, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 909 days.

(21) Appl. No.: 16/990,804

(22) Filed: Aug. 11, 2020

(65) Prior Publication Data

US 2021/0015390 A1 Jan. 21, 2021

Related U.S. Application Data

(63) Continuation of application No. 16/931,567, filed on Jul. 17, 2020, now Pat. No. 11,911,166.
(Continued)

(51) Int. Cl.
*A61N 1/36* (2006.01)
*A61B 5/06* (2006.01)
(Continued)

(52) U.S. Cl.
CPC ............. *A61B 5/366* (2021.01); *A61B 5/068* (2013.01); *A61B 5/283* (2021.01); *A61B 5/339* (2021.01);
(Continued)

(58) Field of Classification Search
CPC .......... A61B 2017/00243; A61B 5/068; A61B 5/283; A61B 5/339; A61B 5/349;
(Continued)

(56) References Cited

U.S. PATENT DOCUMENTS 5,728,140 A 3/1998 Salo et al.
7,177,704 B2 2/2007 Aske et al.
(Continued)

FOREIGN PATENT DOCUMENTS

WO 2008058265 A3 5/2008
WO 2009006325 A1 1/2009

OTHER PUBLICATIONS

Das et al., "NPL Ventricular septal pacing: Optimum Method to position the lead", Indian Heart Journal, Jan. 2018 (Year: 2018).*
(Continued)

*Primary Examiner* — Christopher L Cook

(57) ABSTRACT

A medical device system is configured to guide implantation of a pacing electrode for left bundle branch pacing. The system includes a medical device having a processor configured to receive at least one cardiac electrical signal, determine a feature of the cardiac electrical signal, compare the feature to left bundle branch signal criteria, and determine a left bundle branch signal in response to the feature meeting the left bundle branch signal criteria. The system includes a display unit configured to generate a user feedback signal indicating advancement of a pacing electrode into a left portion of a ventricular septum in response to the processor determining the left bundle branch signal.

29 Claims, 12 Drawing Sheets

Related U.S. Application Data

(60) Provisional application No. 62/876,634, filed on Jul. 20, 2019.

(51) Int. Cl.
| | |
|---|---|
| *A61B 5/283* | (2021.01) |
| *A61B 5/339* | (2021.01) |
| *A61B 5/366* | (2021.01) |
| *A61B 90/00* | (2016.01) |
| *A61N 1/05* | (2006.01) |
| *A61N 1/362* | (2006.01) |
| *A61N 1/365* | (2006.01) |
| *A61B 17/00* | (2006.01) |
| *A61N 1/37* | (2006.01) |
| *A61N 1/372* | (2006.01) |

(52) U.S. Cl.
CPC .............. *A61B 90/37* (2016.02); *A61N 1/056* (2013.01); *A61N 1/362* (2013.01); *A61N 1/36521* (2013.01); *A61B 2017/00243* (2013.01); *A61N 1/371* (2013.01); *A61N 1/372* (2013.01)

(58) Field of Classification Search
CPC ..... A61B 5/366; A61B 5/6846; A61B 5/6847; A61B 5/6869; A61B 5/6885; A61B 5/6886; A61B 5/7271; A61B 90/37; A61N 1/056; A61N 1/08; A61N 1/362; A61N 1/36521; A61N 1/37; A61N 1/371; A61N 1/372; A61N 1/37205; A61N 2001/0585

See application file for complete search history.

(56) References Cited

U.S. PATENT DOCUMENTS

| | | | |
|---|---|---|---|
| 7,529,584 | B2 | 5/2009 | Aske et al. |
| 8,078,287 | B2 | 12/2011 | Liu et al. |
| 8,831,705 | B2 | 9/2014 | Dobak |
| 2011/0213260 | A1 | 9/2011 | Keel et al. |
| 2015/0305695 | A1* | 10/2015 | Lahm ............... G16H 20/40 600/424 |
| 2016/0260210 | A1* | 9/2016 | González ........... G06F 18/23 |
| 2018/0280057 | A1 | 10/2018 | Seifert et al. |
| 2019/0083779 | A1 | 3/2019 | Yang et al. |
| 2019/0083800 | A1 | 3/2019 | Yang et al. |
| 2019/0090951 | A1* | 3/2019 | Camus .............. A61B 8/483 |
| 2019/0111265 | A1 | 4/2019 | Zhou |
| 2019/0111270 | A1 | 4/2019 | Zhou |
| 2020/0037997 | A1* | 2/2020 | Viggen ............. A61B 8/5223 |
| 2020/0101279 | A1 | 4/2020 | Drake et al. |
| 2020/0155798 | A1* | 5/2020 | Yang ................. A61N 1/056 |

OTHER PUBLICATIONS (PCT/US2020/042754) PCT Notification of Transmittal of the International Search Report and the Written Opinion of the International Searching Authority, dated Oct. 11, 2020, 10 pages.

* cited by examiner

METHOD AND APPARATUS FOR IMPLANTATION OF A PACING ELECTRODE

REFERENCE TO RELATED APPLICATION

This application is a continuation of U.S. patent application Ser. No. 16/931,567, filed Jul. 17, 2020, which claims the benefit of U.S. Patent Application No. 62/876,634, filed provisionally on Jul. 20, 2019, both of which are incorporated herein by reference in their entirety.

TECHNICAL FIELD

This disclosure relates to a system for guiding implantation of a cardiac pacing electrode for delivering pacing pulses to a target pacing site.

BACKGROUND

During normal sinus rhythm (NSR), the heartbeat is regulated by electrical signals produced by the sino-atrial (SA) node located in the right atrial wall. Each depolarization signal produced by the SA node spreads across the atria, causing the depolarization and contraction of the atria, and arrives at the atrioventricular (AV) node. The AV node responds by propagating a depolarization signal through the bundle of His of the atrioventricular septum and thereafter to the bundle branches and the Purkinje muscle fibers of the right and left ventricles, sometimes referred to as the "His-Purkinje system."

Patients with a conduction system abnormality, e.g., poor AV node conduction, poor SA node function, or other conduction abnormalities, may receive a pacemaker to restore a more normal heart rhythm and heart chamber synchrony. Ventricular pacing may be performed to maintain the ventricular rate in a patient having atrioventricular conduction abnormalities. A single chamber ventricular pacemaker may be coupled to a transvenous ventricular lead carrying electrodes placed in the right ventricle (RV), e.g., in the right ventricular apex. The pacemaker itself is generally implanted in a subcutaneous pocket with the transvenous ventricular lead tunneled to the subcutaneous pocket. Intracardiac pacemakers have been introduced or proposed for implantation entirely within a patient's heart, eliminating the need for transvenous leads. An intracardiac pacemaker may provide sensing and pacing from within a chamber of the patient's heart, e.g., from within the right ventricle in a patient having AV conduction block.

Dual chamber pacemakers are available which include a transvenous atrial lead carrying electrodes which are placed in the right atrium and a transvenous ventricular lead carrying electrodes that are placed in the right ventricle via the right atrium. A dual chamber pacemaker senses atrial electrical signals and ventricular electrical signals and can provide both atrial pacing and ventricular pacing as needed to promote a normal atrial and ventricular rhythm and promote AV synchrony when SA and/or AV node or other conduction abnormalities are present.

Ventricular pacing via electrodes at or near the right ventricular apex has been found to be associated with increased risk of atrial fibrillation and heart failure. Alternative pacing sites have been investigated or proposed, such as pacing of the His bundle or left bundle branch. Cardiac pacing along the His-Purkinje has been proposed to provide ventricular pacing along the heart's natural conduction system. Pacing the ventricles via the His bundle or left bundle branch, for example, allows recruitment along the heart's natural conduction system, including the bundle branches and the Purkinje fibers, and is hypothesized to promote more physiologically normal cardiac activation than other pacing sites, such as the ventricular apex.

SUMMARY

The techniques of this disclosure generally relate to a medical device system for guiding implantation of a cardiac pacing electrode for delivering ventricular pacing pulses to a target site along the His-Purkinje system, e.g., along the His bundle, which may be along the lower His bundle, or along or in the vicinity of the left bundle branch (LBB) of the His bundle. In some examples, a medical device system operating according to the methods disclosed herein provides audible and/or visual feedback to a clinician or user during the implant procedure for guiding advancement of a pacing electrode into and through the septum for positioning the pacing electrode at a target pacing site and verifying an acceptable implant position. In some examples, the guidance system provides visual and/or audible feedback for guiding a pacing electrode into a left portion of the septum in proximity to the LBB and verifying an acceptable implant position of the pacing electrode for pacing the LBB. The disclosed techniques may include generating feedback signals based on images of the patient's heart using a cardiac imaging unit, analysis of cardiac electrical signals which may include analysis of intracardiac electrogram (EGM) signals and/or electrocardiogram (ECG) signals, pacing capture tests and/or electrode impedance signals.

In one example, the system includes a processor that is configured to receive a cardiac electrical signal, determine at least one feature of the cardiac electrical signal, compare the at least one feature to left bundle branch signal criteria, and determine a left bundle branch signal in response to the at least one feature meeting the left bundle branch signal criteria. The system further includes a display unit configured to generate a user feedback signal indicating advancement of a pacing electrode into a left portion of a ventricular septum in response to the processor detecting the left bundle branch signal.

In another example, the system performs a method including receiving a cardiac electrical signal, determining at least one feature of the cardiac electrical signal, comparing the at least one feature to left bundle branch signal criteria, determining a left bundle branch signal in response to the feature meeting the left bundle branch signal criteria, and generating a user feedback signal indicating advancement of a pacing electrode into a left portion of a ventricular septum in response to detecting the left bundle branch signal.

In another example, a non-transitory computer readable medium stores instructions which, when executed by a processor of a medical device system, cause the system to determine at least one feature of a cardiac electrical signal, compare the at least one feature to left bundle branch signal criteria, determine a left bundle branch signal in response to the at least one feature meeting the left bundle branch signal criteria, and generate a user feedback signal indicating advancement of a pacing electrode into a left portion of a ventricular septum in response to determining the left bundle branch signal.

In another example, a medical device system includes an imaging unit configured to generate a cardiac image including an image of a ventricular septum. The system includes a processor configured to generate a septal boundary line superimposed on the cardiac image, generate a marker intersecting the septal boundary line and superimposed on the cardiac image to indicate an left bundle branch (LBB) target implant region for a pacing electrode, and generate a user feedback signal to guide advancement of the pacing electrode into the LBB target region according to the marker location on the cardiac image. The system may further include a processor configured to receive a cardiac electrical signal, determine at least one feature of the cardiac electrical signal, compare the at least one feature to left bundle branch signal criteria, and determine a left bundle branch signal in response to the at least one feature meeting the left bundle branch signal criteria. The system may further include a display unit configured to generate a user feedback signal indicating advancement of the pacing electrode into a left portion of a ventricular septum in response to the processor determining the left bundle branch signal.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
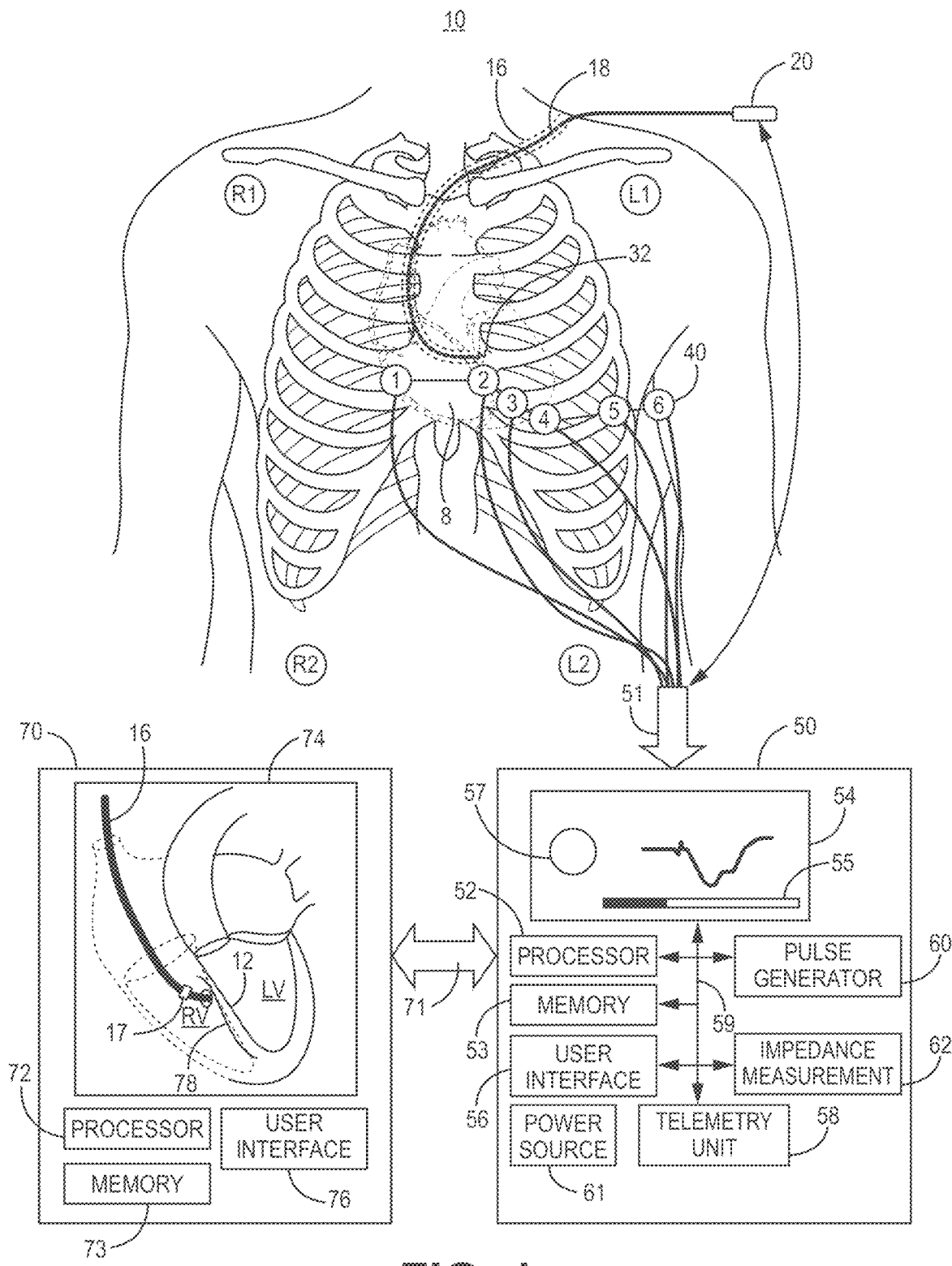
FIG. 1 is a conceptual diagram of a medical device system capable of sensing and analyzing cardiac electrical signals, generating a cardiac image and generating user feedback signals for guiding pacing electrode implantation according to one example.

A medical device system configured to process and analyze cardiac electrical signals and/or cardiac images during cardiac pacing electrode implantation is described herein. The system is configured to generate feedback signals to a user during the electrode implantation. The feedback signals may include generated visual representations and/or audible signals which may represent a relative location of a pacing electrode to a desired pacing site. The feedback signals may be adjusted based on the cardiac electrical signal analysis, electrode impedance signals, pacing capture tests, and/or cardiac images acquired during the implantation procedure to indicate when a pacing electrode has reached a targeted pacing site and/or when the pacing electrode is not at a targeted pacing site. For example, when a pacing electrode is being implanted for delivering LBB pacing, cardiac electrical signal analysis is performed by the medical device system as the pacing electrode is advanced into the ventricular septum from the right ventricle. Feedback signals are generated and adjusted to notify the user when the cardiac electrical signals correspond to a pacing electrode position within the right ventricular portion of the septum and/or when the cardiac electrical signals correspond to a pacing electrode position within the left ventricular portion of the septum.

As used herein, the term "LBB pacing" refers to delivery of pacing pulses to or in the vicinity of the His bundle or LBB such that at least the LBB is captured by the pacing pulses. Accordingly a "LBB pacing site" or "LBB pacing location" may refer to a location in the tissue adjacent to the His-Purkinje system. The LBB pacing site may be accessed from the right ventricular septum such that a pacing electrode may be advanced toward the LBB pacing site.

Pacing of the LBB provides conduction along the heart's native conduction system and may improve ventricular synchrony. However, deployment of a pacing electrode to a pacing site for delivering LBB pacing is challenging because the pacing electrode may not be advanced far enough into the septum to achieve LBB pacing, e.g., positioned nearer the right ventricular border of the septum than the left ventricular border. In other instances, the pacing electrode may be over advanced through the septum into the left ventricular chamber, causing perforation of the left ventricular border of the septum. Because pacing of the LBB can promote a more physiologically normal electrical and mechanical activation of the heart, proper placement of a pacing electrode for LBB pacing can improve the performance of the pacing system for clinically benefiting the patient. It is to be understood that guiding placement of a pacing electrode for LBB pacing may include guiding placement of the pacing electrode for pacing of the His bundle, or at least the distal portion of the His bundle, which includes pacing of the LBB.

The system and techniques disclosed herein provide various improvements in a medical device system configured to generate and display various electrical parameters that a user may rely on when implanting a pacing electrode. The techniques disclosed herein improve the function of an external device in guiding a pacing electrode implant procedure by performing cardiac signal sensing, processing and analysis and generating user feedback signals based thereon to inform a user of a pacing electrode location and confirm that a target location, e.g., in the left portion of the interventricular septum for achieving LBB pacing, has been reached.

The techniques disclosed herein therefore provide improvements in the computer-related field of surgical guidance having practical applications in positioning a pacing electrode. By providing a medical device generating user feedback signals according to the techniques herein, the complexity and likelihood of human error in positioning a pacing electrode at a desirable pacing site is reduced. The techniques disclosed herein may enable a pacing electrode, which may be a lead-based or housing-based electrode as described in the examples below, to be positioned with a high degree of confidence at a pacing site along the heart's native conduction system in a manner that is simplified, flexible, and patient-specific.

FIG. 1 is a conceptual diagram of a medical device system 10 capable of sensing and analyzing cardiac electrical signals, generating a cardiac image and generating user feedback signals for guiding pacing electrode implantation according to one example. The pacing electrode may be a lead-based electrode, e.g., pacing electrode 32 carried by lead 18 as shown in FIG. 1, or a housing-based electrode of a leadless intracardiac pacemaker as described below in conjunction with FIG. 3. In FIG. 1, cardiac pacing lead 18 is shown advanced within a patient's heart 8 for positioning pacing electrode 32 within the ventricular septum at an LBB pacing site. The system 10 includes an external device 50 for receiving and analyzing cardiac electrical signals during the pacing electrode implantation procedure. External device 50 may be embodied as a programmer used in a hospital, clinic or physician's office to acquire and analyze cardiac signals. External device 50 may alternatively be embodied as a handheld device or pacing system analyzer. External device 50 may receive ECG signals from one or more cutaneous or subcutaneous electrodes. In the example shown, ECG electrodes 40 including cutaneous electrodes 1-6 along with the four limb leads (R1, L1, R2 and L2) may be placed for acquiring a 12-lead ECG by external device 50. Additionally or alternatively, external device 50 may generate an EGM signal from cardiac electrical signals received via pacing lead 18. Pacing lead 18 may be electrically coupled to external device 50 for providing raw cardiac electrical signals received via electrode 32 paired with another sensing electrode.

External device 50 may include an electrode/lead interface 51 for receiving input from ECG electrodes 40 and/or lead 18, processor 52, memory 53, display unit 54, user interface unit 56, telemetry unit 58, pulse generator 60 and impedance measurement unit 62. Processor 52 is configured for processing cardiac electrical signals received from ECG electrodes 40 and/or pacing lead 18 for generating ECG and/or EGM signals, respectively. Processor 52 is configured to analyze the ECG and/or EGM signals for detecting signal features indicative of the location of pacing electrode 32 within the interventricular septum. Based on the signal analysis, processor 52 may determine a pacing electrode location relative to the native conduction system and generate user feedback signals based on the determined location. Processor 52 may be coupled to the other components and units of external device 50, e.g., via a data bus 59, for controlling the functions attributed to external device 50 herein. For example, processor 52 may pass generated ECG and/or EGM signals and user feedback signals to a display unit 54, control pulse generator 60 to generate pacing pulses, control impedance measurement unit 62 to perform an electrode impedance measurement, etc.

Processor 52 executes instructions stored in memory 53. Processor 52 may include any one or more of a microprocessor, a controller, a digital signal processor (DSP), an application specific integrated circuit (ASIC), a field-programmable gate array (FPGA), or equivalent discrete or analog logic circuitry. In some examples, processor 52 may include multiple components, such as any combination of one or more microprocessors, one or more controllers, one or more DSPs, one or more ASICs, or one or more FPGAs, as well as other discrete or integrated logic circuitry. The functions attributed to processor 52 herein may be embodied as software, firmware, hardware or any combination thereof.

Memory 53 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 53 may be configured to store instructions executed by processor 52 for obtaining and analyzing cardiac signals for determining a location of a pacing electrode relative to cardiac structures, such as the LBB. Memory 53 may store cardiac signal features determined by processor 52 for use in determining when the signal features meet LBB signal criteria indicative of pacing electrode placement at an LBB pacing site.

Display unit 54, which may include a liquid crystal display, light emitting diodes (LEDs) and/or other visual display components, may generate a display of the ECG and/or EGM signals and/or data derived therefrom. Display unit 54 may be configured to generate a graphical user interface (GUI) including various windows, icons, user selectable menus, etc. to facilitate interaction by a user with the external device 50. Display unit 54 may function as an input and/or output device using technologies including liquid crystal displays (LCD), quantum dot display, dot matrix displays, light emitting diode (LED) displays, organic light-emitting diode (OLED) displays, cathode ray tube (CRT) displays, e-ink, or monochrome, color, or any other type of display capable of generating tactile, audio, and/or visual output. In some examples, display unit 54 is a presence-sensitive display that may serve as a user interface device that operates both as one or more input devices and one or more output devices.

In some examples, display unit 54 may generate a visual implant progress indicator 55 in response to data signals from processor 52 indicating the progress made in advancing pacing electrode 32 toward an LBB pacing site. Implant progress indicator 55 may include an advancing bar, arrow, wheel or other icon or a variable speed blinking icon, variable speed blinking LED or other visual indicator of the progress made in advancing pacing electrode 32 from the right border of the interventricular septum toward a left portion of the septum to an LBB pacing site. In some examples, user feedback generated and displayed by display unit 54 may include a report of the results of cardiac electrical signal analysis. Parameters determined from the signal analysis, such as shape of intrinsic QRS or evoked response morphology, intrinsic QRS or evoked response duration (width), right and/or left ventricular activation time data, or other parameters determined or detected from the cardiac electrical signals, may be reported to the user as quantitative values or qualitative indicators (e.g., increased, decreased, RBB block pattern, LBB block pattern, etc.).

In other examples, display unit 54 may produce an output to a user in another fashion, such as via a sound card, video graphics adapter card, speaker, one or more USB interfaces, video and/or audio output interfaces, or any other type of device capable of generating audio, video, or other output. For instance, display unit 54 may include a speaker 57 configured to generate an audible implant progress indicator in response to signals from processor 52. The audible implant progress indicator may be a variable speed beeping sound or tone that changes in frequency and/or tone as the pacing electrode 32 is advanced closer to or arrives at an LBB pacing site within the left portion of the interventricular septum. Audible user feedback signals generated by display unit 54 and broadcast by speaker 57 may include voiced notifications, e.g., indicating an electrode location or recommending advancement or retraction of the pacing electrode 32. Various user feedback signals described herein may be generated as visual, audible or a combination of visual and audible feedback signals.

User interface unit 56 may include a mouse, touch screen, keypad or the like to enable a user to interact with external device 50, e.g., to initiate and terminate an implant session, adjust settings of display unit 54, or make other user requests. Telemetry unit 58 includes a transceiver and antenna configured for bidirectional communication with a telemetry circuit included in an implantable pacemaker, which may be coupled to pacing lead 18 after pacing electrode 32 is deployed to an acceptable LBB pacing site. Telemetry unit 58 is configured to operate in conjunction with processor 52 for sending and receiving data relating to pacemaker functions via a wireless communication link with the implantable pacemaker.

External device 50 may include a pulse generator 60 for generating and delivering pacing pulses via lead 18 during the implant procedure. As described below, post-pace ECG and/or EGM signals may be analyzed for determining when LBB signal criteria are met for detecting implantation of pacing tip electrode 32 at an acceptable LBB pacing site. In some examples, external device 50 may control pulse generator 60 to generate pacing pulses to perform ventricular capture tests during the electrode implantation procedure for verifying the location of one or more electrodes within the septum. Pulse generator 60 may include one or more holding capacitors charged to a pacing pulse voltage amplitude by a power source 61 of external device 50. The holding capacitor(s) may be coupled to an output capacitor via switching circuitry to deliver the pacing pulse to pacing electrode 32 (and a return anode electrode) as the holding capacitor(s) are discharged for a selected pacing pulse width.

In some examples, external device 50 may include an impedance measurement unit 62 which may include a drive circuit for generating a drive current or voltage signal for measuring the pacing electrode impedance. The drive current or voltage signal may be applied to pacing tip electrode 32 and a return anode electrode, which may be an electrode carried by lead 18 (e.g., return anode electrode 34 shown in FIG. 2) or another available cutaneous or subcutaneous electrode. Impedance measurement unit 62 may receive a resulting voltage or current signal in response to applying the drive signal and may use the resulting signal as an impedance measurement signal or convert the resulting signal to an impedance signal by determining the impedance based on the applied drive signal and measured signal. A low impedance may indicate that the pacing tip electrode 32 is in a blood volume rather than within septal tissue, e.g., within the RV chamber prior to advancement into the septum 12 or in the left ventricular chamber due to over advancement and perforation through the septum 12 into the left ventricle (LV). Impedance measurements may be performed by external device 50 for confirming an acceptable LBB pacing site location of pacing tip electrode 32 as described below.

External device 50 includes a power source 61 that is coupled to the various units of external device 50 for providing power to unit circuits and components as needed. Power source 61 may include one or more rechargeable or non-rechargeable batteries or may be coupled to an external power source, such as plugged into an electrical outlet.

System 10 may include an imaging unit 70 capable of generating an image of heart 8 on imaging display unit 74. As described below, the generated image may include markers or images of cardiac landmark structures such as the right ventricular septum and the location of pacing electrode 32 and/or pacing lead 18 relative to cardiac structures. Imaging unit 70 may be a fluoroscopy unit or echocardiography unit as examples. A catheter 16 may be advanced within heart 8 during the pacing lead implantation procedure to guide the distal end of pacing lead 18 and pacing electrode 32 to a location along the RV border of the interventricular septum 12 as represented in the image on imaging display unit 74. A catheter 16 may be used to deliver contrast dye for visualizing the location of the distal end of the pacing lead 18 and pacing electrode 32 relative to cardiac structures such as the RV septal border and the ring of the tricuspid valve annulus.

Imaging unit 70 may include a processor 72, memory 73 and user interface 76. In some examples, imaging unit 70 may be in communication with external device 50 via data link 71 for providing imaging data to processor 52. Processor 72 and/or processor 52 may be configured individually or cooperatively to execute firmware or software stored in imaging unit memory 73 and/or external device memory 53 for automatically generating cardiac structure landmark markers on the cardiac image generated by imaging display unit 74 to guide a user in advancing pacing electrode 32. For example, an RV septal boundary marker 78 may be automatically generated by system 10 to provide a user with a visual marker of the RV septal border. The boundary marker 78 may be automatically generated by execution of an algorithm stored in memory 73 or 53 that determines the RV septal border location based on contrast between pixels corresponding to blood or contrast dye in the RV and the septal tissue, for example. Other cardiac structure landmark markers that may be generated automatically or in response to user input received via user interface 76 or display unit 74 may correspond to the tricuspid valve annulus and/or tricuspid septal leaflet or other landmark cardiac structures that may guide the user in navigating and advancing a pacing electrode toward a septal entry point and to a desired pacing site, which may be along the LBB or other portion of the native conduction system such as along the His bundle or a distal portion of the His bundle.

As described below, the location of the pacing electrode 32 as it is advanced through the septum 12 may be tracked by imaging unit 70 and external device 50 based on analysis of ECG and/or EGM signals during an intrinsic (non-paced) ventricular rhythm and/or during delivery of pacing pulses via pacing electrode 32. The atria may or may not be paced during the non-paced ventricular rhythm; however, ventricular pacing is not being delivered. In some examples, external device 50 may additionally or alternatively perform pacing capture tests and/or impedance measurements using pacing electrode 32 and in some cases an anode ring electrode as described below for generating data indicative of the location of pacing electrode 32 during advancement in interventricular septum 12.

Since the location of the pacing electrode 32 within septum 12 relative to the LBB and the LV septal border may not be discernable from the image on display 74, analysis of ECG signals, EGM signals, pacing capture tests, and/or impedance signals is performed by external device processor 52 to enable external device processor 52 to generate user feedback signals to guide advancement of pacing electrode 32 to an acceptable LBB pacing site. The user feedback signals may include the visual progress indicator 55, an audible progress indicator generated by speaker 57, visual markers generated on imaging display unit 74 of imaging unit 70, text or voiced notifications or graphical images generated on external device display unit 54 or any combination thereof.

Figure 2:
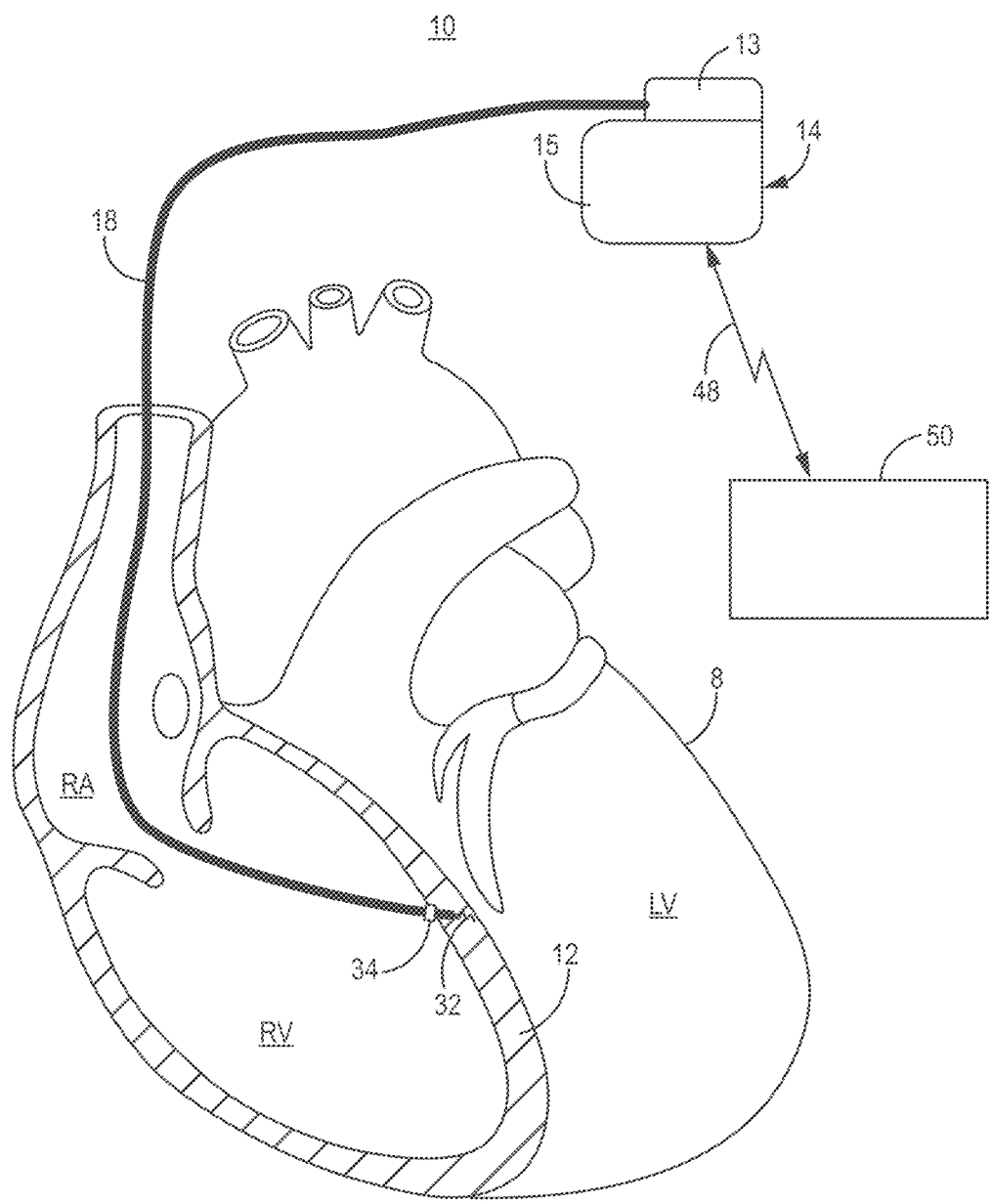
FIG. 2 is a conceptual diagram of a pacing lead coupled to an implantable pacemaker capable of pacing a patient's heart and sensing cardiac electrical signals.

In some examples, the catheter 16 or other delivery tool used to implant pacing electrode 32 may include a return anode electrode 17 (seen in the image on imaging display unit 74) for use in combination with the pacing electrode 32 for sensing cardiac signals, performing pacing capture tests, and/or acquiring a pacing electrode impedance signal during implantation of pacing electrode 32. Lead 18 may include one or more ring electrodes that may be selected for use as a return anode electrode, as shown in FIG. 2. However, in some instances an anode electrode carried proximally along lead 18 may be insulated within the body of catheter 16 or another delivery tool such that it is not available during the implant procedure. In this case, catheter 16 may carry one or more electrodes, such as ring electrode 17, for use as an anode electrode paired with pacing electrode 32. In other examples, any of ECG electrodes 40 or another dedicated cutaneous or subcutaneous electrode may be provided and coupled to external device 50 via interface 52 to serve as a return anode in combination with pacing electrode 32 during the implant procedure.

FIG. 2 is a conceptual diagram of pacing lead 18 coupled to an implantable pacemaker 14 capable of pacing a patient's heart 8 and sensing cardiac electrical signals via lead 18. After pacing tip electrode 32 is positioned at an acceptable pacing site under the guidance of system 10 (as described in greater detail below), lead 18 may be coupled to an implantable pacemaker, such as pacemaker 14, for delivery of ventricular pacing pulses at the desired pacing site, e.g., the LBB. Pacemaker 14 is shown as a single chamber device capable of delivering ventricular pacing pulses and sensing electrical signals in the ventricles. In other examples, pacemaker 14 may be a dual chamber device configured to receive an atrial pacing and sensing lead, which may be positioned in the right atrial chamber for delivering atrial pacing pulses and sensing atrial electrical signals. In still other examples, pacemaker 14 may be a multi-chamber pacemaker or biventricular pacemaker, including a right atrial pacing and sensing lead and/or right ventricular pacing and sensing lead positioned in the RV for delivering RV pacing pulses and sensing cardiac electrical signals from within the RV, which may be in addition to lead 18.

Pacemaker 14 includes a housing 15, which may be hermetically sealed, to enclose internal circuitry corresponding to the various circuits and components for sensing cardiac signals from heart 8 and controlling electrical stimulation therapy, e.g., pacing therapy, delivered by pacemaker 14. Pacemaker 14 includes a connector block 13 coupled to housing 15 including at least one lead connector bore configured to receive the proximal end (lead connector 20 shown in FIG. 1) of pacing lead 18. Connector block 13 may have additional connector bores for optionally receiving an atrial pacing and sensing lead and/or RV pacing and sensing lead in other examples. Lead 18 may be advanced transvenously into the RV via the RA for positioning pacing and sensing electrodes 32 and 34 within the interventricular septum 12. In particular, pacing tip electrode 32 is advanced within the septum 12 from the RV toward the LV to position tip electrode 32 at an LBB pacing site in some examples. Pacing tip electrode 32 may be a helical "screw-in" electrode that may be rotatably advanced into the septum 12, e.g., by rotation of the proximal lead connector 20 (shown in FIG. 1). A ring electrode 34 may be spaced proximally from pacing tip electrode 32 and may be used as the return anode electrode with the cathode tip electrode 32 for delivering pacing pulses and for sensing ventricular electrical signals.

While lead 18 is described herein as being deployed in the interventricular septum 12 for LBB pacing, it is recognized that techniques disclosed herein may be adapted for monitoring advancement of pacing tip electrode 32 through cardiac tissue at other locations based on processing and analysis of cardiac electrical signals, pacing capture tests, electrode impedance signals and/or cardiac images to enable generation of user feedback signals to guide implantation of pacing tip electrode 32 at a desired pacing site. As described below in conjunction with the various flow charts and diagrams presented herein, a change in a feature of a cardiac electrical signal during an intrinsic rhythm and/or following pacing pulses may be indicative of the cardiac tissue adjacent pacing tip electrode 32. As such, analysis of cardiac electrical signals by external device processor 52 enables external device 50 to generate user feedback signals to indicate when pacing tip electrode 32 is adjacent cardiac tissue targeted for pacing therapy delivery. In the illustrative examples presented herein, the targeted cardiac tissue for pacing therapy delivery is the LBB, however in other examples the targeted cardiac tissue may be the right bundle branch (RBB), His bundle, distal portion of the His bundle, Purkinje fibers, AV node, or other cardiac tissue site.

The electrodes 32 and 34 are coupled to respective insulated conductors extending within the elongated, insulative body of ventricular lead 18. Each connector provides electrical connection of a respective electrode 32 or 34 to the proximal lead connector 20 (seen in FIG. 1). Proximal lead connector 20 provides connectability to external device 50, e.g., using electrical connectors such as alligator clips or other types of electrical connectors and wires, via electrode/lead interface 51. After confirmation of the location of pacing electrode 32 at a desired pacing site, based on output displayed by external device 50, proximal lead connector 20 may be coupled to connector block 13 of pacemaker 14, and thereby to circuitry enclosed within pacemaker 14.

As described below in conjunction with FIG. 4, cardiac electrical signal sensing circuitry included in pacemaker 14 may receive a cardiac electrical signal from electrodes 32 and/or 34 of pacing lead 18 for sensing ventricular signals including R-waves attendant to ventricular depolarization. Electrodes 32 and 34 may be selected in a bipolar ventricular sensing electrode pair or one electrode carried by pacing lead 18, e.g., tip electrode 32 or ring electrode 34, may be used in combination with pacemaker housing 15 for receiving a unipolar, ventricular signal for sensing R-waves by cardiac electrical signal sensing circuitry.

It is to be understood that although pacemaker 14 is illustrated in FIG. 2 as a pacemaker capable of delivering ventricular pacing via lead 18, pacemaker 14 may be configured as an implantable cardioverter defibrillator capable of delivering both low voltage cardiac pacing therapies and high voltage cardioversion and defibrillation (CV/DF) shocks. In this case, pacemaker 14 may be coupleable to at least one lead carrying at least one high voltage CV/DF electrode such as an elongated coil electrode, which may be carried by lead 18 in addition to pacing and sensing electrodes 32 and 34.

Pacemaker 14 is shown in telemetric communication with external device 50 by a communication link 48. Communication link 48 may be established between pacemaker 14 and external device 50 using a wireless radio frequency (RF) link such as BLUETOOTH®, Wi-Fi, or Medical Implant Communication Service (MICS) or other RF or communication frequency bandwidth or communication protocols. Data stored or acquired by pacemaker 14, including physiological signals or associated data derived therefrom, results of device diagnostics, and histories of detected rhythm episodes and delivered therapies, may be retrieved from pacemaker 14 by external device 50 following an interrogation command. In some examples, in addition to the pacing electrode implant guidance techniques described herein, external device 50 may be used in a hospital, clinic or physician's office to retrieve data from pacemaker 14 and to program cardiac signal sensing parameters, cardiac rhythm detection parameters and therapy control parameters used by pacemaker 14 in sensing the heart rhythm and delivering pacing therapies.

Figure 3:
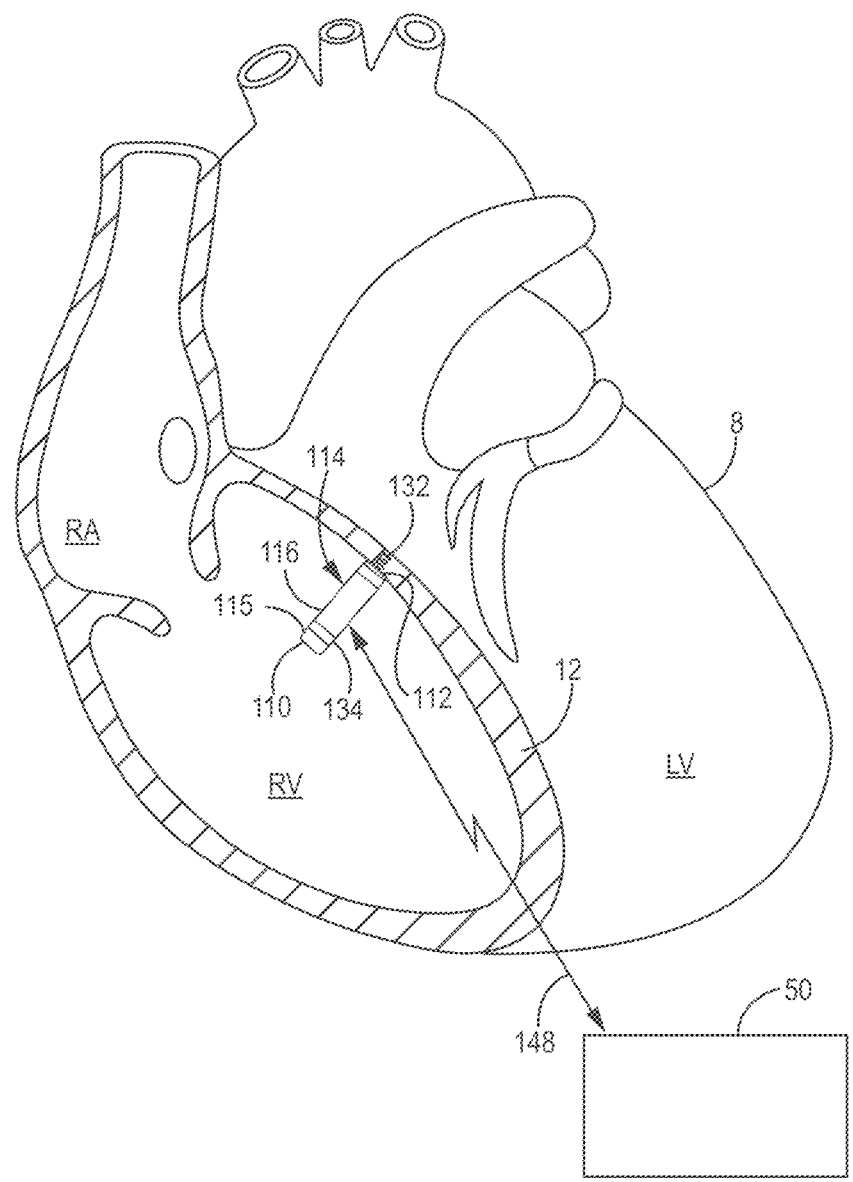
FIG. 3 is a conceptual diagram of a leadless intracardiac pacemaker positioned within the right ventricle for providing ventricular pacing via the LBB.

FIG. 3 is a conceptual diagram of a leadless intracardiac pacemaker 114 positioned within the RV for providing LBB pacing according to one example. The techniques disclosed herein for guiding pacing electrode implantation may be used in conjunction with implanting a leadless pacemaker, such as pacemaker 114, having a pacing electrode coupled to and extending from the pacemaker housing, without an intervening medical lead. Pacemaker 114 may include an elongated housing 115 having a longitudinal sidewall 116 extending from a housing proximal end 110 to a housing distal end 112. Pacemaker 114 is shown to include a pacing electrode 132 extending from a distal end 112 of pacemaker housing 115. Pacing electrode 132 may be referred to as a "distal tip electrode" and is shown as a "screw-in" helical electrode, extending away from distal end 112 of the pacemaker housing 115. Pacemaker 114 further includes an anode electrode, which may be along distal end 112 or located more proximal from pacing electrode 132. In the example shown, a proximal electrode 134, which may circumscribe all or a portion of the longitudinal sidewall 116 of the housing 115, may be provided as a return anode electrode. In other examples, a return anode electrode used in sensing and pacing may be positioned on housing proximal end 110 or on housing distal end 112 and may be a button, ring or other type of electrode. Pacing of the LBB (or along the His bundle) may be achieved using the distal pacing electrode 132 as the cathode electrode and the proximal electrode 134 as the return anode.

Intracardiac pacemaker 114 may be implanted in the RV of the patient's heart 8 with pacing electrode 132 advanced into interventricular septum 12 for delivery of pacing pulses to the LBB or along the distal His bundle, for example. As disclosed herein, a user may be guided by user feedback signals to an appropriate septal entry site of the pacing electrode 132 generated by imaging display unit 74 and/or external device display unit 54 based on cardiac image processing by imaging unit 70 and/or cardiac electrical signal processing by external device 50, respectively. For example, a user may be guided to insert the pacing electrode 132 into septum 12 in a target region marked on a cardiac image displayed by imaging unit 74 that is approximately 10 to 20 millimeters below the tricuspid valve annulus, as identified by imaging unit processor 72. A proximal portion of the pacing electrode 132 may be electrically insulated, e.g., with a coating, such that only a distal portion of pacing electrode 132, furthest from pacemaker housing distal end 112, is exposed to provide targeted pacing at a tissue site that includes the LBB.

Pacing electrode 132 may be an active fixation electrode, e.g., a helical electrode, providing fixation to anchor the pacemaker 114 at the implant position. In other examples, pacing electrode 132 may be formed having a straight shaft with a distal active electrode portion or other type of electrode that is advanceable through the interventricular septum 12 to deliver pacing in a left portion of the septum 12. In some examples, pacemaker 114 may include a fixation member that includes one or more tines, hooks, barbs, helices or other fixation member(s) that anchor the distal end of the pacemaker 114 at the implant site and may not function as an electrode. Examples of leadless intracardiac pacemakers that may be used in conjunction with the techniques described herein are generally disclosed in commonly-assigned U.S. Publication No. 2019/0111270 (Zhou) and U.S. Publication No. 2019/0083800 (Yang, et al.), both of which are incorporated herein by reference in their entirety.

Cardiac electrical signals produced by heart 8 may be sensed by pacemaker 114 using electrodes 132 and 134. The raw cardiac electrical signal received via electrodes 132 and 134 may be processed by sensing and control circuitry included in pacemaker 114, e.g., as described below in conjunction with FIG. 4, for producing an EGM signal. The EGM signal may be transmitted wirelessly to external device 50 via communication link 148. The EGM signal may be further processed and analyzed by the processor 52 of external device 50 for determining a location of pacing electrode 132, e.g., within septum 12 relative to the LBB, using the techniques disclosed herein. In some examples, pacemaker 114 may be configured to perform a pacing capture test and/or an electrode impedance signal may be acquired using pacing electrode 132 for confirming a location of pacing electrode 132 within septum 12. Pacing capture test data and/or impedance data produced by pacemaker 114 may be transmitted to external device 50 for use in generating user feedback signals during advancement of pacing electrode 132 and/or for confirming a desired pacing site.

Pacemaker 114 may be advanced into the RV and to an implant site along the right border of septum 12 using a delivery tool, e.g., a catheter or other tool that facilitates pushing and/or rotation of pacemaker 114 for advancing pacing electrode 132 into the interventricular septum. Examples of leadless intracardiac pacemaker delivery tools that may be used in conjunction with the techniques described herein are disclosed in commonly-assigned U.S. Publication No. 2020/0101279 (Drake, et al.) and in U.S. Publication No. 2018/0280057 (Seifert et al.), both of which are incorporated herein by reference in their entirety. As described above in conjunction with FIG. 1, the catheter or delivery tool used to implant pacing electrode 132 may include at least a return anode electrode in some examples for use in combination with the pacing electrode 132 for sensing cardiac signals, performing pacing capture tests, and/or acquiring an impedance signal when the proximal electrode 134 is enclosed within the delivery tool and unavailable for use as a return anode. In other examples, the delivery tool may include two or more electrodes used in sensing and/or delivering test pulses during advancement of the delivery tool toward a targeted implant site.

Figure 4:
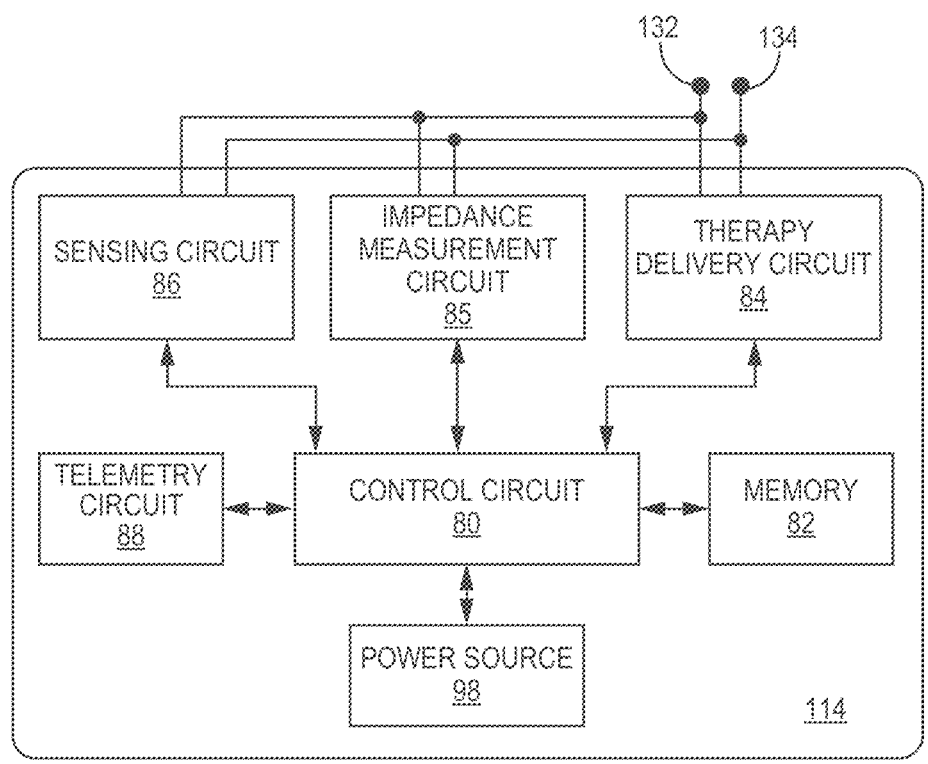
FIG. 4 is a schematic diagram of circuitry that may be enclosed within a medical device configured to sense cardiac electrical signals and deliver pacing pulses according to one example.

FIG. 4 is a schematic diagram of circuitry that may be enclosed within an implantable pacemaker configured to deliver pacing pulses and sense cardiac electrical signals according to one example. The block diagram of FIG. 4 is described with reference to pacemaker 114 carrying electrodes 132 and 134 for the sake of illustration, but it is to be understood that the functionality attributed to the various circuits and components shown in FIG. 4 may correspond to circuitry enclosed in pacemaker 14 of FIG. 2, which may be coupled to lead 18 carrying pacing electrode 32 and ring electrode 34.

The electronic circuitry enclosed within housing 115 includes software, firmware and hardware that cooperatively monitor cardiac electrical signals, determine when a pacing therapy is necessary, and deliver electrical pacing pulses to the patient's heart as needed according to programmed pacing mode and pacing pulse control parameters. The electronic circuitry includes a control circuit 80, memory 82, therapy delivery circuit 84, sensing circuit 86, telemetry circuit 88 and power source 98.

Power source 98 provides power to the circuitry of pacemaker 114 including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86, and 88 are to be understood from the general block diagram of FIG. 4 but are not shown for the sake of clarity. For example, power source 98 may be coupled to one or more charging circuits included in therapy delivery circuit 84 for providing the power needed to charge holding capacitors included in therapy delivery circuit 84 that are discharged at appropriate times under the control of control circuit 80 for delivering pacing pulses. Power source 98 is also coupled to components of sensing circuit 86, such as sense amplifiers, analog-to-digital converters, switching circuitry, etc., telemetry circuit 88 and memory 82 to provide power to the various components and circuits as needed.

The functional blocks shown in FIG. 4 represent functionality included in pacemaker 114 (or pacemaker 14) and may include any discrete and/or integrated electronic circuit components that implement analog and/or digital circuits capable of producing the functions attributed to pacemaker 114 (or pacemaker 14) herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern cardiac medical device system, given the disclosure herein, is within the abilities of one of skill in the art.

Control circuit 80 communicates, e.g., via a data bus, with therapy delivery circuit 84 and sensing circuit 86 for cooperatively sensing cardiac electrical signals and controlling delivery of cardiac electrical stimulation therapies in response to sensed cardiac events, e.g., R-waves attendant to ventricular depolarization, or the absence thereof. Electrodes 132 and 134 (or in the case of pacemaker 14, electrodes 32 and 34 and housing 15) may be electrically coupled to therapy delivery circuit 84 for delivering electrical stimulation pulses and to sensing circuit 86 for sensing cardiac electrical signals produced by the heart, including both intrinsic signals (such as intrinsic R-waves) produced by the heart in the absence of a pacing pulse that captures the heart and evoked response signals following a delivered pacing pulse of sufficient energy to cause cardiac capture.

Sensing circuit 86 may include an input filter for receiving a cardiac electrical signal from a pair of sensing electrodes, e.g., electrodes 132 and 134, a pre-amplifier, an analog-to-digital converter and a bandpass filter for producing a multi-bit digital cardiac electrical signal, which may be referred to as an "EGM" signal when the raw signal is sensed from within a heart chamber. Features of the EGM signal produced by sensing circuit 86 may be determined by control circuit 80 for use in determining the location of pacing electrode 132 within the ventricular septum. The EGM signal and/or data derived therefrom may be transmitted to external device 50 for further processing and analysis for detecting a location of pacing electrode 132 for use in guiding the pacing electrode implant procedure as described below.

Upon detecting a cardiac electrical event based on a sensing threshold crossing, sensing circuit 86 may produce a sensed event signal that is passed to control circuit 80. For example, a ventricular event detector may produce an R-wave sensed event signal in response to an R-wave sensing threshold crossing. The sensed event signals are used by control circuit 80 for setting pacing escape interval timers that control the basic time intervals used for scheduling cardiac pacing pulses. Control circuit 80 may include various timers or counters for counting down a pacing interval. A sensed event signal may trigger or inhibit a pacing pulse depending on the particular programmed pacing mode. While pacemakers 14 and 114 are shown as single chamber ventricular pacemakers in FIGS. 2 and 3, respectively, it is recognized that the techniques disclosed herein may be performed in conjunction with implantation of a dual chamber or multi-chamber pacemaker system including atrial pacing and/or sensing capabilities for providing atrial synchronous ventricular pacing, for example. A pacemaker that is coupled to a pacing electrode implanted using the techniques disclosed herein may be configured for delivering ventricular bradycardia pacing therapy, atrial synchronized ventricular pacing, rate responsive pacing, cardiac resynchronization therapy (CRT), anti-tachycardia pacing therapy or other pacing therapies, which may include pacing the ventricles via the LBB or the His bundle including the LBB.

Therapy delivery circuit 84 may include charging circuitry, one or more charge storage devices such as one or more holding capacitors, an output capacitor, and switching circuitry that controls when the holding capacitor(s) are charged and discharged across the output capacitor to deliver a pacing pulse via pacing electrode 132 (or electrode 32) coupled to the therapy delivery circuit 84 and a selected return anode electrode, e.g., electrode 134 (or electrode 34 or housing 15 of pacemaker 14). Charging of a holding capacitor to a programmed pacing voltage amplitude and discharging of the capacitor for a programmed pacing pulse width may be performed by therapy delivery circuit 84 according to control signals received from control circuit 80. For example, a pace timing circuit included in control circuit 80 may include programmable digital counters set by a microprocessor of the control circuit 80 for controlling the basic pacing time intervals associated with various single chamber or dual chamber pacing modes, CRT or anti-tachycardia pacing sequences. The microprocessor of control circuit 80 may also set the amplitude, pulse width, polarity or other characteristics of the cardiac pacing pulses, which may be based on programmed values stored in memory 82.

Control circuit 80 may control therapy delivery circuit 84 to deliver a pacing pulse to perform a pacing capture test during the implant procedure for use in determining a position of pacing electrode 132 and/or proximal electrode 134. As described below, a pacing capture test may be performed using pacing electrode 132 as the cathode electrode and proximal electrode 134 as the return anode (or another available catheter-based, cutaneous or subcutaneous electrode). In some examples, a pacing capture test may be performed using proximal electrode 134 (or ring electrode 34) as the cathode electrode to determine when the proximal electrode 134/34 is in contact with or within septum 12.

Pacemaker 114 may include an impedance measurement circuit 85 for applying a drive signal to a selected electrode, e.g., pacing electrode 132 or proximal electrode 134, and recording a resultant signal indicative of the electrode impedance. When an electrode is within the blood pool of the RV or LV, the electrode impedance is very low compared to the electrode impedance when the electrode is within the interventricular septum. As such, relative changes in electrode impedance may be detected for determining when an electrode, e.g., pacing electrode 132 or proximal electrode 134, is within the RV blood pool, within the septum, or over-advanced into the LV blood pool.

Telemetry circuit 88 includes a transceiver and antenna for communicating with an external device 50 (FIG. 1) using radio frequency communication or other communication protocols as described above. Control parameters utilized by control circuit 80 for sensing cardiac events and controlling pacing therapy delivery may be programmed into memory 82 via telemetry circuit 88. Under the control of control circuit 80, telemetry circuit 88 may receive downlink telemetry from and send uplink telemetry to the external device 50. Telemetry circuit 88 may be used to transmit an EGM signal acquired using pacing electrode 132 or data derived therefrom, a pacing electrode impedance signal or data derived therefrom, and/or a pacing capture test result. External device 50 may receive the data transmitted by telemetry circuit 88 for use in generating user feedback signals during the pacing electrode implant procedure. During an implant procedure, external device 50 may transmit a request to control circuit 80 via telemetry circuit 88 to acquire an EGM signal, an impedance signal, and/or perform a pacing capture test and transmit corresponding signals or data derived therefrom for use in generating visual and/or audible feedback representative of the location of pacing electrode 132 and/or proximal electrode 134.

Figure 5:
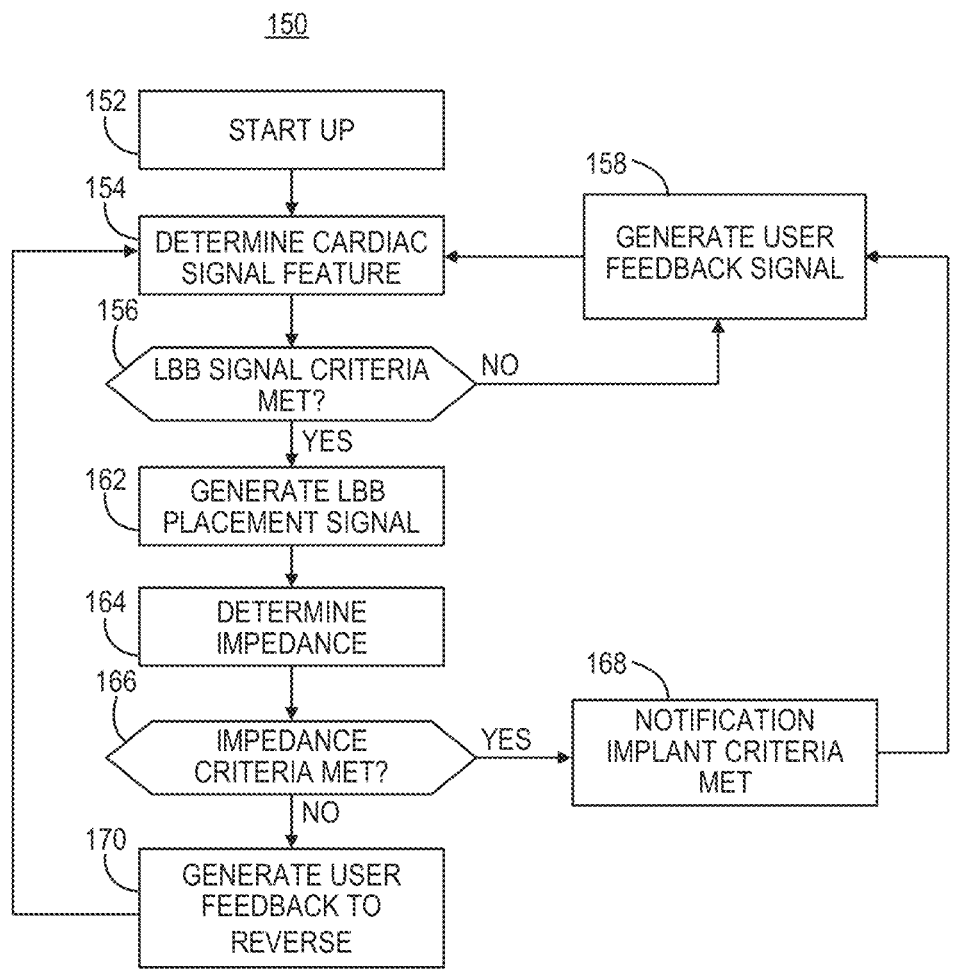
FIG. 5 is a flow chart of a method performed by the system of FIG. 1 for guiding implantation of a pacing electrode according to one example.

FIG. 5 is a flow chart 150 of a method for guiding implantation of a pacing electrode performed by system 10 of FIG. 1 according to one example. The process shown by flow chart 150 represents operations that external device 50 may perform to guide implantation of the pacing electrode once it is advanced to a location at or near the RV septal wall. As described below, imaging unit 70 may be used prior to the pacing electrode reaching the RV septal wall to provide user guidance in navigating the pacing electrode to a target location along the septal wall. In some examples, imaging unit 70 may generate a visual representation of the pacing electrode or a delivery catheter or other delivery tool relative to the RV septal wall, which may include an angle of advancement relative to a cardiac landmark, to guide insertion of the pacing electrode into the RV septum and toward the target LBB pacing site. The process of flow chart 150 may be initiated at block 152 once the pacing electrode 32/132 has been advanced transvenously toward or into the heart, e.g., within the RV near the septal border, but is not yet advanced into the septum 12.

At block 152, external device 50 may perform a start-up process in response to a user initiating the implant guidance procedure, e.g., via user interface 56. The start-up process may include generating ECG signals and/or EGM signals from electrical signals received via ECG electrodes 40 and/or electrodes 32 and 34 from lead 18 or electrodes 132 and 134 from pacemaker 114. In some examples, the EGM signals may be received by the external device telemetry unit 58 from an intracardiac pacemaker such as pacemaker 114 as described above. The ECG and/or EGM signals may be displayed on external device display unit 54.

During the start-up process at block 152, processor 52 may determine one or more ECG and/or EGM signal features to determine baseline cardiac electrical signal features prior to the pacing electrode (e.g., lead-based pacing electrode 32 or housing-based pacing electrode 132) being advanced into the septum 12. The start-up process at block 152 may additionally or alternatively include determining a baseline impedance using the pacing electrode 32/132 and a selected return electrode. Since a proximal ring electrode 34/134 may be within a delivery catheter or other tool, an alternative return electrode, e.g., a cutaneous or subcutaneous electrode, may be selected as the return anode in combination with pacing electrode 32 for acquiring an impedance signal. In some examples, an electrode carried by the delivery catheter or other tool, e.g., electrode 17 of catheter 16 (FIG. 1), may be used as the return anode for acquiring an impedance signal.

The start-up process at block 152 may include generating and displaying a notice or instructions to a user. A user notification instructing advancement against the ventricular septum may be generated. In some examples, external device processor 52 may control pulse generator 60 to deliver a pacing pulse via the pacing electrode 32 and a selected return anode electrode during the start-up process at block 152. The pacing pulse is delivered at a pulse energy that is expected to at least capture myocardial tissue. In the case of pacemaker 114, therapy delivery circuit 84 may deliver one or more pacing pulses in response to a pacing command transmitted from external device 50 to pacemaker 114. Processor 52 may determine that myocardial capture has occurred in response to a delivered pacing pulse, based on an analysis of an EGM or ECG signal. Determination of capture indicates that the pacing electrode 32/132 is against the ventricular septum. When capture does not occur, the pacing electrode may still be in the RV blood pool. The user notification instructing advancement of the electrode against the ventricular septum may continue to be generated when capture is not detected (and/or the ECG/EGM signature indicating a position at the RV septal border is not detected). In some examples, the user notification may instruct the user to adjust the relative angle of the pacing electrode or delivery catheter relative to the RV septal border or other cardiac landmark and or adjust the pacing electrode position along the RV septum. The ECG signal following a pacing pulse when the pacing electrode is in contact with the RV septum may be detected by processor 52 as a "W-wave" morphology in ECG lead V1, corresponding to an LBB block pattern (representing right bundle branch pacing). When the "W" shaped waveform is detected in response to a pacing pulse, processor 52 may determine that the pacing electrode is at a target septal entry site for advancing the electrode into the septum for LBB pacing. Accordingly, in some examples, capture detection by processor 52 may be followed by a user notification that the electrode 32/132 is in contact with the septal wall.

Once evidence of the pacing electrode being against the septum is detected by processor 52, which may be based on a change in impedance, a change in the ECG or EGM signal, or detection of pacing pulse capture or user input verification, the processor 52 may generate and display a user notification instructing the user to advance the pacing electrode, e.g., by rotating the proximal connector assembly 20 of lead 18 by a predetermined number of turns, for instance two to three or more clockwise turns. In the example of FIG.

3, the pacemaker 114 may be rotated using a delivery tool to advance a pacing electrode 132 into the septum 12.

At block 154, processor 52 may determine one or more cardiac signal features from ECG and/or EGM signals as the pacing electrode 32/132 is advanced. In other examples, processor 52 may determine one or more cardiac signal features after receiving a user input indicating that the pacing electrode has been advanced the predetermined number of turns per the instructions displayed by the external device 50. The signal feature(s) is/are compared to LBB signal criteria at block 156. LBB signal criteria are discussed in conjunction with FIGS. 4-6 below.

The term "LBB signal" as used herein refers to a signal that is indicative of a pacing electrode location within a left portion of the interventricular septum. The LBB signal may be detected from a cardiac electrical signal, e.g., an ECG signal or an EGM signal, during an intrinsic ventricular rhythm or following a ventricular pacing pulse. The term "LLB signal criteria" refers to criteria applied by processor 52 to at least one ECG signal and/or the EGM signal for detecting an ECG and/or EGM signal waveform, pattern or feature that is expected to occur when the pacing electrode is in the left portion of the septum. For example, LBB signal criteria may include criteria for detecting an intrinsic LBB potential signal, an injury current based on elevated baseline amplitude after the LBB potential signal, the LV intrinsic activation time between the LBB potential signal and QRS maximum peak being within an LBB signal range, the LV paced activation time from a pacing pulse to the evoked response peak being within an LBB signal range, and/or any of the changes in the ECG signals described below that occur in the pacing-induced evoked response as the pacing electrode 32 is advanced from the right portion to the left portion of the septum 12.

In some examples, processor 52 may analyze the EGM signal generated from signals received via lead 18 (or from pacemaker 114) to detect an LBB signal as an LBB potential signal. The LBB potential signal is a signal spike occurring in the EGM signal immediately preceding a QRS signal attendant to the depolarization of the ventricular myocardium. The LBB potential signal represents the electrical potential conducted along the LBB during an intrinsically conducted ventricular beat that leads to ventricular myocardial depolarization. In one example, if the LBB potential signal is not detected, LBB signal criteria may be unmet at block 156. In other examples, other LBB signal criteria may be applied to detect a position of the pacing electrode at an LBB pacing site. In a patient that does not have LBB block, an LBB potential signal may be detected from the EGM signal during an intrinsic (non-paced) ventricular rhythm. In other cases, if the patient has LBB block, the LBB potential signal may be detected during an escape beat.

However, when LBB block is present such that an intrinsic LBB potential signal is not present and/or the LBB potential signal accompanying intrinsic conduction along the LBB cannot be detected, pacing pulses may be delivered by the pacing electrode and the post-pace ECG and/or EGM signals may be analyzed to determine when LBB signal criteria are met. If the LBB signal criteria are unmet at block 156, processor 52 may generate a user feedback signal at block 158. The user feedback signal generated at block 158 may include adjusting a visual progress indicator 55, e.g., by advancing the progress indicator by a portion that indicates incomplete pacing electrode advancement, and/or adjusting an audible progress indicator, e.g., by increasing a rate or tone of audible signals. The user feedback signal may be a notification generated by display unit 54 to advance the pacing electrode by one or more turns or continue slow advancement of the pacing electrode. Processor 52 may be configured to analyze cardiac electrical signals as the pacing electrode is advanced so that the clinician does not need to stop and wait for a feedback signal before advancing the pacing electrode further. In some examples, processor 52 may generate a user feedback signal to indicate that advancement should stop if the pacing electrode is advanced into the left ventricular blood pool. Over advancement may be detected by processor 52 based on a sudden change in the ECG/EGM signal, loss of capture, or a sudden decrease in pacing impedance.

When processor 52 determines that LBB signal criteria are met at block 156, processor 52 may generate a user feedback signal that indicates that LBB pacing site placement of the pacing electrode is detected at block 162. The feedback signal may be advancement of the visual progress indicator 55 to a completed state, e.g., a green or other colored or shaded bar, circle or other visual representation of the advancement progress may be filled indicating 100% advancement. The feedback signal may include an adjustment of an audible signal, which may be a change in tone, a change in a rate of beeps, a voiced communication or other signal representative of successful positioning of the pacing electrode at an LBB pacing site. The feedback signal may include a text notification displayed by display unit 54 indicating that an LBB signal has been detected.

In some examples, the pacing electrode guidance process may be complete upon determining that LBB signal criteria are met and the LBB placement signal is generated at block 162. In other examples, when processor 52 determines LBB signal criteria are met, processor 52 may perform additional analysis of cardiac signals for confirming the LBB pacing site placement of the pacing electrode 32/132. For instance, processor 52 may control impedance measurement unit 62 to determine an electrode impedance at block 164 using the pacing electrode 32 and a selected return anode electrode. The impedance may be compared to an impedance threshold at block 166. The threshold may be set to a predetermined, default or nominal threshold value corresponding to a minimum expected impedance when the pacing electrode is within septal tissue and not in the blood pool. The threshold may be set based on a previously determined impedance in some examples. For instance, a baseline impedance determined during the start-up process at block 152, prior to advancement of the pacing electrode into the ventricular septum, may be an impedance threshold for detecting over-advancement of the pacing electrode into the LV blood pool. When the impedance is within a threshold range of the baseline impedance, over-advancement may be detected. In another example, a pacing electrode impedance may be determined during advancement in the septum before an LBB signal is detected, e.g., when the EGM and/or ECG signal analysis indicates a right or mid-septal location of the pacing electrode, as described below. This impedance is an indication of the pacing electrode impedance that is expected when the pacing electrode remains within the septum. A threshold drop in impedance from this impedance determined during advancement may indicate over-advancement into the LV blood pool.

When the impedance is determined by processor 52 to be low, e.g., less than a predetermined impedance threshold, similar to a baseline RV blood pool impedance, or less than a previous impedance measurement determined during advancement within the septum, the pacing electrode may be over-advanced and perforated into the LV chamber. When the pacing electrode impedance is determined to be low, therefore, processor 52 determines that impedance criteria are unmet at block 166 and may generate a user feedback signal at block 170 to indicate that the pacing electrode may be over advanced and should be reversed or retracted. For example, display unit 54 may generate a display at block 170 indicating that LV perforation may have occurred. The progress indicator 55, for example, may represent over-advancement by extending a bar beyond a 100% advancement limit with the portion extending beyond the 100% advancement displayed in red. Processor 52 may generate other visual output representative of the impedance data and/or over-advancement determination which may include a representation of the pacing impedance being low or out of range. Processor 52 may further generate a voiced or textual over-advancement warning on display unit 54. Processor 52 may generate a user feedback instruction for display on display unit 54 to retract or rotate pacing electrode counter-clockwise, which may specify to retract by at least one or more turns, e.g., 3 to 4 turns, to withdraw the pacing electrode back into the left portion of the septum 12.

When the pacing electrode impedance is too low, processor 52 may continue to determine cardiac signal features at block 154 in order to re-determine that LBB signal criteria are met at block 156 and verify that the pacing electrode impedance criteria are met at block 166. Processor 52 may be configured to generate user feedback signals as needed throughout this process. Determination that the LBB signal criteria are met at block 156 and determination that the impedance criteria are met at block 166 are shown to be performed sequentially in FIG. 5. It is to be understood, however, that such determinations may be made concurrently, in parallel operations, or in a different order than shown here. When both the LBB signal criteria are met and the pacing electrode impedance criteria are met, processor 52 and display unit 54 may generate a user feedback signal at block 168 indicating that the LBB pacing site criteria are met. The user feedback signal may include an adjustment of a visual and/or audible progress indicator and/or a text or voice notification indicating that the pacing electrode is positioned for LBB pacing.

Figure 6:
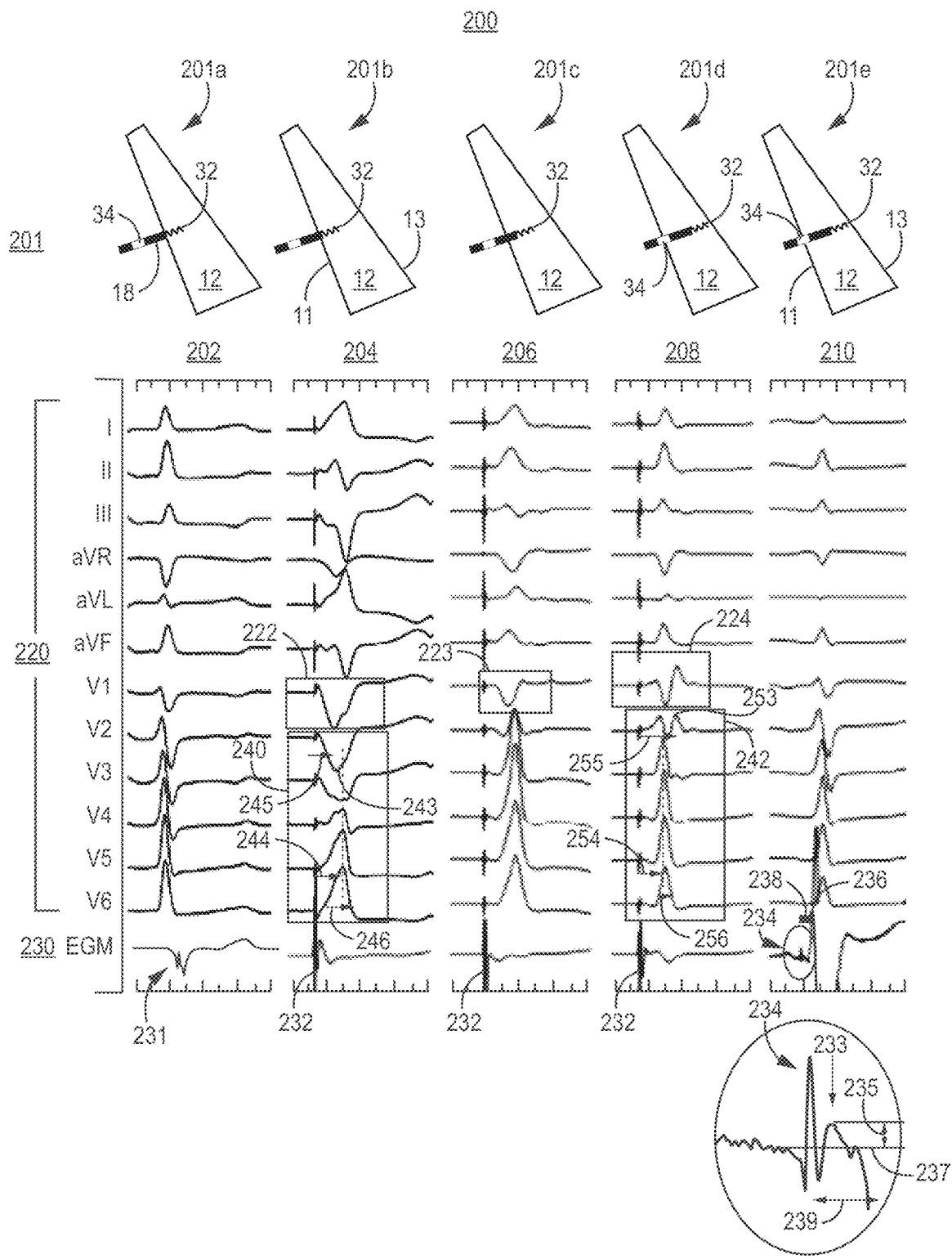
FIG. 6 is a diagram of ECG and EGM signals that may be generated from sensed cardiac electrical signals for display to a user and analyzed by a processor of the system of FIG. 1 for generating user feedback signals during a pacing electrode implant procedure.

FIG. 6 is a diagram of sensed ECG and EGM signals that may be generated as output by processor 52 for display to a user by external device 50 and analyzed by processor 52 to guide pacing electrode advancement. In FIG. 6, each column 202, 204, 206, 208, and 210 represents the ECG signal 220 and EGM signal 230 that may be sensed and displayed when the pacing electrode 32/132 is at a corresponding location within the ventricular septum as depicted in diagrams 201. Diagrams 201 at the top of each column 202-210 illustrate the approximate depth of the pacing electrode 32 within the ventricular septum corresponding to the ECG or EGM signal waveforms shown in the column below.

Moving left to right, the pacing electrode 32 is initially in the right portion of septum 12, near the right septal border 11 as shown by diagram 201*a*, and advances into the left portion of septum 12 without perforating left septal border 13, as shown by diagram 201*e*. The first column 202 depicts ECG signals 220 and EGM signal 230 sensed while pacing electrode 32 is in the right portion of septum 12 during an intrinsic ventricular rhythm (no pacing). An intrinsic QRS waveform 231 may be sensed by the pacing electrode 32 from the right septum. The second column 204 depicts ECG signals 220 and EGM signal 230 when a pacing pulse is delivered using the pacing electrode 32 positioned in the right septum as shown in diagram 201*b*.

As shown by the diagram 201*c* above column 206, the ECG signals 220 and EGM signal 230 in column 206 correspond to a pacing electrode location that is approximately mid-way within the septum 12, between the right and left portions of the septum. The ECG signals 220 and the EGM signal 230 depicted in column 206 represent the signals that may be analyzed and displayed by external device 50 when the pacing electrode 32 is used to deliver a pacing pulse in the inter-ventricular septum. Column 208 depicts ECG signals 220 and EGM signal 230 that are sensed when a pacing pulse is delivered by the pacing electrode 32 in the left septum as indicated by the diagram 201*d*. Column 210 depicts ECG signals 220 and EGM signal 230 sensed during an intrinsic (non-paced) ventricular rhythm when the pacing electrode 32 is advanced into the left portion of septum 12 as shown in diagram 201*e*. The columns 208 and 210 represent ECG signals 220 and EGM signal 230 when pacing electrode 32 is in the vicinity of the LBB for delivering LBB pacing.

Processor 52 may apply criteria for detecting an LBB signal that indicates a pacing electrode location in the left portion of the ventricular septum 12 to a cardiac electrical signal, e.g., an EGM signal 230 and/or one or more of ECG signals 220 obtained during a paced rhythm. Additionally or alternatively, processor 52 may apply criteria for detecting an LBB signal to the EGM signal 230 obtained during the intrinsic heart rhythm. In FIG. 6, the first column 202 and last column 210 of 12-lead ECG signals 220 and the EGM signal 230 are examples of signals that may be analyzed by processor 52 during an intrinsic ventricular rhythm. The EGM signal 230 may be generated from a raw cardiac electrical signal received via pacing tip electrode 32 and the return ring electrode 34 or another available return anode electrode. The EGM signal 230 in column 202 is an intrinsic signal received via the pacing electrode in the right portion of the ventricular septum. Column 202 may represent the cardiac electrical signals that may be presented to a user on display unit 54 when pacing electrode 32/132 is first advanced into the septum 12.

The EGM signal 230 in column 210 represents a signal that may be presented to a user on display unit 54 and/or analyzed by processor 52 after advancement of the pacing electrode into the left portion of the septum 12. When the pacing electrode 32/132 is positioned in the left portion of the septum 12, the EGM signal 230 presents an LBB potential signal 234 followed by a relatively large amplitude intrinsic QRS signal 236. The presence of the LBB potential signal 234 in the EGM signal 230 sensed using the pacing electrode 32/132 is evidence that the pacing electrode 32 is positioned in proximity to the LBB and well-positioned for LBB pacing. Accordingly, in some examples, processor 52 analyzes the EGM signal 230 as the user advances the pacing electrode into and across the ventricular septum 12. Processor 52 may analyze the EGM signal 230 until an LBB potential signal 234 is detected. One method for detecting the LBB potential signal 234 as an LBB signal is described below in conjunction with FIG. 12.

Additionally or alternatively, the time interval 238 from the LBB potential signal spike 234 to the maximum positive peak of the QRS signal 236 is determined by processor 52. When the LBB potential signal 234 is detected by processor 52 and an intrinsic QRS signal 236 is detected by processor 52 within a threshold time interval, e.g., within 10 to 40 ms, an LBB signal is detected by processor 52 as evidence of LBB pacing site placement of tip electrode 32/132.

In other examples, an injury current signal may be detected by processor 52 based on analysis of the EGM signals 230 sensed during an intrinsic ventricular rhythm using the pacing electrode 32/132. An elevated post-potential signal amplitude 233, immediately following LBB potential signal 234 (see the inset, enlarged diagram of LBB potential signal 234), is evidence of injury current. An elevated post-potential amplitude 233 is therefore an indication that the pacing electrode 32/132 has entered the left portion of the septum 12, causing local injury near the LBB.

Processor 52 may detect the injury current by determining and storing a baseline amplitude 237 (which may be an average baseline) determined prior to detecting the LBB potential signal 234 and determining the maximum amplitude 233 within an injury current detection window 239 following the LBB potential signal 234. The injury current detection window extends up to 10 ms, up to 20 ms, or up to 25 ms, as examples, after detection of the LBB potential signal 234. Processor 52 may determine the post-potential amplitude difference 235 as the difference between the maximum post-potential amplitude 233 (after LBB potential signal 234) and pre-potential amplitude 237 (prior to LBB potential signals 234). When this difference 235 of the EGM signal amplitude just prior to the LBB potential signal 234 and just after the LBB potential signal 234 is greater than a threshold amplitude difference or percentage change, e.g., at least 0.1 to 1 millivolt difference between pre-potential amplitude 237 and the post-potential amplitude 233, an injury current and associated LBB potential signals 234 may be detected by processor 52 as a LBB signal meeting LBB signal criteria, indicating a left septal location of the pacing electrode 32/132.

In response to detecting the LBB potential signal 234 and/or the injury current based on the amplitude difference 235, processor 52 may generate or adjust a user feedback signal indicating placement of the pacing electrode 32/132 within a left portion of septum 12 in proximity to the LBB, with or without any further processing or analysis of cardiac electrical signals for verifying the LBB pacing site placement of the pacing electrode 32/132. While processor 52 is referred to as performing the detection of an injury current, LBB potential signal 234 and other EGM signal features determined in the disclosed techniques, it is to be understood that one or more processors included in the implantable pacemaker, e.g., in control circuit 80 shown in FIG. 4, and/or the external processor 52 may individually or cooperatively perform the processing, analysis and detection steps disclosed herein in a distributed manner.

In some examples, in addition or alternatively to analyzing the intrinsic EGM signal during pacing electrode advancement, processor 52 may control pulse generator 60 to deliver pacing pulses 232 via the pacing electrode 32 with a selected return anode (or send a pacing command to pacemaker 114 to deliver a pacing pulses via pacing electrode 132) and analyze one or more ECG signals 220 and/or EGM signal 230 for detecting an LBB signal.

When the pacing electrode 32/132 is within the right portion of the septal wall 12, relatively more proximate to the right septal border 11 than the left septal border 13 (e.g., as shown in diagram 201b), capture in the right portion of the ventricular septum 12 may occur resulting in a relatively wide, negative polarity V1 ECG signal 222. The wide negative polarity signal corresponding to capture in the right side of the septum 12 may have a characteristic "W" shape in the V1 ECG signal 222 and may correspond to an ECG signal that is observed when LBB block is present. The characteristic, wide, negative "W" shaped signal is a "LBB block-like signal" because the pacing evoked depolarization caused by delivering a pacing pulse in the right ventricular septum occurs rapidly in the right side of the septum 12 and is conducted later to the left ventricular myocardium, similar to the condition of LBB block. As the pacing electrode is advanced further into the inter-ventricular septum, as shown by diagram 201c, the characteristic "W" shape of the V1 ECG signal corresponding to LBB block disappears and is replaced by an evoked response signal 223 (in column 206) having a relatively narrower negative polarity waveform.

When the pacing electrode 32/132 is advanced further into the left ventricular septum, proximate to the left septal border 13 as shown by diagram 201d, the evoked response signal 224 in the V1 ECG signal due to capture of the LBB may characteristically include a relatively narrow negative peak followed by a relatively narrow positive peak. This morphology of a narrow negative peak followed by a narrow positive peak is similar to the ECG morphology expected in a patient having RBB block and is therefore a "RBB block-like signal" that occurs when LBB pacing capture occurs and is therefore an LBB signal pattern. Processor 52 may be configured to perform morphology waveform analysis of the ECG evoked response waveforms following a delivered pacing pulse 232 for detecting this transition from a "W" shaped negative polarity evoked response waveform 222 to a single-peaked negative polarity evoked response waveform 223 to the narrow negative polarity followed by narrow positive polarity waveform 224 during advancement of the pacing electrode 32/132 through the ventricular septum 12 while delivering pacing pulses 232 via the pacing electrode (cathode) 32/132 and a selected return anode electrode, which may be a catheter or delivery tool electrode or a surface (cutaneous) electrode.

The evoked response morphology in the V1 ECG signal following an LBB pacing pulse that captures the LBB may resemble an RBB block ECG signal morphology because the RBB is not captured by the pacing pulse. An RBB block pattern may exhibit an rSR morphology or QR or S wave morphology. As such, an overall evoked response waveform morphology analysis may be performed by processor 52 to determine an LBB signal when an RBB block-like signal morphology in the V1 (or V2) ECG signal following a pacing pulse delivered by the pacing electrode 32/132. Morphology analysis may include time domain amplitude analysis, wavelet transform analysis, or frequency domain analysis. Examples of variousV1 ECG signal features that may be determined and tracked during advancement of the pacing electrode 32/132 across the ventricular septum 12 while delivering pacing pulses are described below in conjunction with FIG. 7.

Other ECG signals may be analyzed by processor 52 in addition to or instead of the V1 ECG signal. Processor 52 may analyze an ECG signal, e.g., the V5 and/or V6 ECG signals, to determine the LV activation time 244 from pacing pulse 232 to a maximum peak amplitude of the evoked response signal following the pacing pulse. LV activation time 244 may be determined as the pacing electrode location is advanced across the septum 12. The LV activation time 244 when the pacing electrode 32/132 is in the right portion of septum 12 (column 204) is relatively long and undergoes a decrease to a relatively rapid LV activation time 254 as the pacing electrode 32/132 is advanced into the left portion of septum 12 (column 208). The LV activation time from pacing pulse 232 to a maximum peak amplitude of the evoked response signal decreases when the pacing electrode is in the left portion of the septum because the LBB is captured early after the pacing pulse. The myocardial depolarization resulting of LBB capture is conducted to the RV relatively later, after LBB capture, resulting in a longer RV activation time 255 observed in the V2 ECG signal compared to the LV activation time 254. The longer RV activation time due to later conduction to the RV myocardium is also observed as a later peak 253 in the V1 or V2 ECG signals compared to the maximum peak of the V5 or V5 ECG signals corresponding to earlier LV activation. The time interval 254 from the pacing pulse 232 to the maximum peak of the post-pace evoked response signal is relatively short, e.g., 70 to 90 ms, in the V5 or V6 ECG signal (more proximate the LV) and relatively longer or delayed, e.g., greater than 90 ms, in the V1 or V2 ECG signals (more proximate the RV). In some examples, the time interval 255 from the pacing pulse 232 to the maximum peak of the evoked response signal, also referred to herein as the "RV activation time," in the V1 and/or V2 signal may be compared to the LV activation time 254 in the V5 and/or V6 signal. An ECG signal having a relatively short LV activation time in the V5 or V6 ECG signal caused by LBB capture compared to relatively longer RV activation time 253 in the V1 or V2 ECG signal caused by delayed activation of the right ventricle following LBB capture may be determined by processor 52 as an LBB signal indicative of a left septal location of the pacing electrode 32/132 and may be determined a.

In other examples, a relative shortening of the LV activation time 246 to LV activation time 256 in the V5 and/or V6 ECG signals, as the pacing electrode is advanced from the right to the left portion of the septum 12, may be detected by processor 52 as an LBB signal. Additionally or alternatively, a relative increase in the RV activation time 245 to RV activation time 255 in the V1 or V2 ECG signals as the pacing electrode 32/132 is advanced may be detected by processor 52 as an LBB signal. A change from a shorter RV activation time 245 to a longer RV activation time 255 determined from the V1 or V2 ECG signals, a change from a longer LV activation time 244 to a shorter LV activation time 254 determined from the V5 or V6 ECG signals, and/or a change from a positive difference between the LV activation time 244 less the RV activation time 245 (column 204) to a negative difference between LV activation time 254 less RV activation time 255 (column 208) may be determined by processor 52 as a change to an LBB signal evidencing proximity of the pacing electrode 32/132 to the LBB.

As shown in FIG. 6, the evoked response waveforms 242 during pacing in the left portion of the septum 12 in each of the V2 through V6 ECG signals (column 208) undergo changes in polarity, signal width, maximum positive peak amplitude, activation time interval from the pacing pulse to the maximum positive peak, and/or other morphological changes compared to the respective evoked response waveforms 240 during pacing in the right portion of the septum 12 (column 204). For example, the V2 ECG signal changes from a relatively wide, negative polarity signal, which may have the "W" shaped morphology, when the pacing electrode 32/132 is in the right portion of the septum 12 to a "notched" signal (resembling an "M" shaped morphology), having two positive peaks separated by a negative peak, when the pacing electrode 32/132 is in the left portion of the septum 12. Processor 52 may be configured to detect this "notched" morphology from the V2 ECG signal as a RBB block-like signal that is evidence of pacing the LBB, resulting in early capture and activation of the LBB followed by conduction to the RV. Morphological changes are also observed in ECG leads I, II, III, aVR, aVL and aVF between columns 204 and 208 corresponding to pacing in the right portion and left portion of the septum 12, respectively. As such, processor 52 may be configured to receive raw cardiac electrical signals from all or a selected combination of 12-lead surface electrodes for analyzing and determining features from one or more of the ECG signals to detect an LBB signal corresponding to pacing and capture at an LBB pacing site, which may resemble an RBB block-like ECG signal.

Detection of an LBB signal indicative of the pacing electrode 32/132 being in an LBB pacing position may be made by processor 52 based on detecting a change in a post-pace evoked response signal in one selected ECG signal, e.g., either V1 or V6, that resembles an LBB block QRS signal (indicating pacing in the right portion of the septum) to a post-pace evoked response signal that resembles an RBB block QRS signal (indicating pacing in the left portion of the septum). For example, the wide evoked response width 246 (characteristic of LBB block) in the ECG V5 or V6 signals during pacing in the right septum decreases to a relatively narrow evoked response width 256 during pacing in the left septum indicating LBB block correction and LBB capture. Additionally or alternatively, processor 52 may perform a comparative analysis between two or more different ECG signals, e.g., comparing the V1 or V2 ECG signals to the V5 or V6 ECG signals to detect differences in the RV and LV activation times or other evoked response signal features that are indicative of a RBB block-like signal in the V1 or V2 ECG signals and/or correction of LBB block as evidenced by a narrow evoked response width 256 and/or early LV activation time 254 in the V5 or V6 ECG signals. Example methods of LBB signal detection by processor 52 are described below in conjunction with FIG. 12.

In still other examples, the EGM signal 230 may be analyzed during pacing pulse delivery using the pacing electrode 32/132 as a pacing cathode electrode for detecting an LBB signal during advancement in septum 12. Example techniques for detecting an LBB signal from EGM signal 230 during pacing pulse delivery are described below in conjunction with FIG. 8. When processor 52 determines that the LBB signal detection criteria based on one or any combination of ECG signal(s) and/or the EGM signal analysis during pacing pulse delivery, processor 52 may generate a user feedback signal indicating that LBB pacing placement of the pacing electrode 32/132 is indicated.

Processor 52 may additionally analyze the EGM signal 230 during an intrinsic ventricular rhythm (non-paced) for detecting the LBB potential signal 234 and/or an injury current based on the amplitude difference 235 as described above for determining an LBB signal and confirming LBB pacing site placement of the pacing electrode 32/132. In other examples, processor 52 may determine an intrinsic LV activation time 238 from the EGM signal 230 by detecting the LBB potential signal 234 and the maximum peak 236 of the evoked QRS signal. When the intrinsic LV activation time 238 is less than a threshold interval (or within a threshold activation time interval range), the processor 52 may detect an LBB signal indicative of left septal position of the pacing electrode 32/132. Techniques for determining an LBB pacing location of the pacing electrode 32/132 using the EGM signal 230 may be used in a patient that does not have LBB block.

Figure 7:
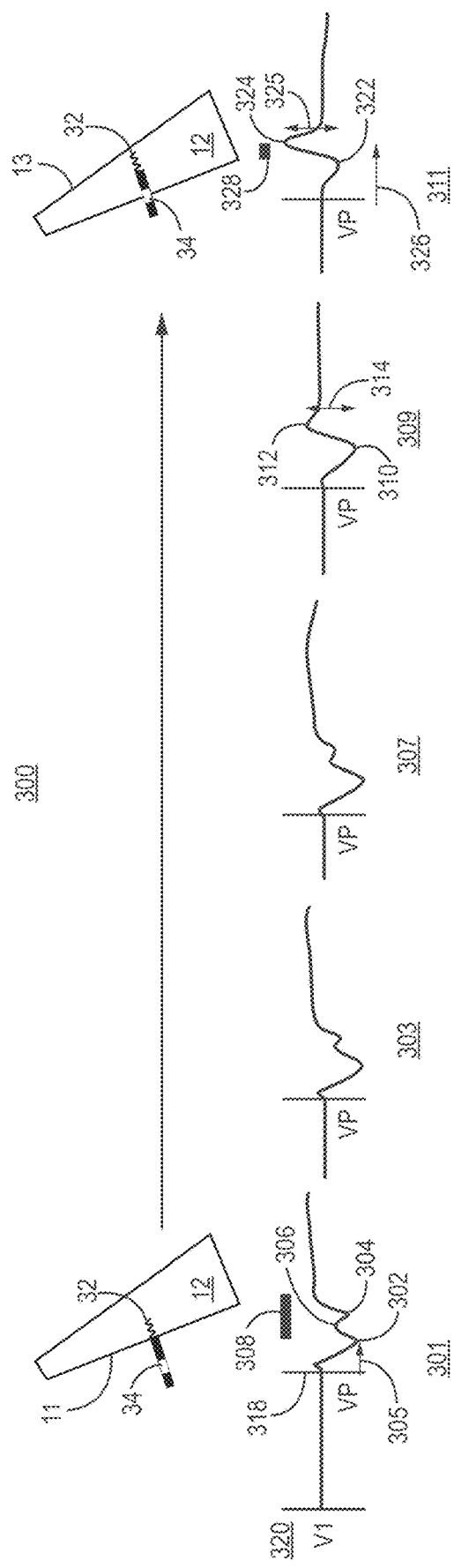
FIG. 7 is a diagram of a V1 ECG signal during advancement of a pacing electrode from a position proximate the right border of the ventricular septum to a position proximate the left border of the ventricular septum.

FIG. 7 is a diagram 300 of a V1 ECG signal 320 during advancement of the pacing electrode 32/132 from a position proximate the right border 11 of ventricular septum 12 to a position proximate the left border 13 of septum 12 (as indicated by arrow 301). Example evoked response waveforms 301, 303, 307, 309 and 311 as they may appear in the V1 ECG signal 320 are shown as the pacing electrode 32/132 progresses from an initial position in the right portion of the septum 12 (waveform 301) to a final position in the left portion of the septum 12 (waveform 311) with intermediate septal positions corresponding to evoked response waveforms 303, 307 and 309.

As observed in the example of FIG. 7, the evoked response waveform 301 in the V1 signal 320 exhibits a characteristic "W" shape, with two negative peaks 302 and 304 and intervening inflection point 306, when the pacing electrode 32 is in the right portion of the septum 12. Processor 52 may be configured to determine evoked response waveform features as the pacing electrode 32 is advanced through the septum 12 for detecting the transition from the characteristic W-shaped, relatively wide negative polarity waveform 301 to a loss of the "W" shape in the single, relatively wide negative peak of intermediate evoked response waveform 309, and subsequently to the narrow negative peak followed by the narrow positive peak evoked response waveform 311 when the pacing electrode 32 is positioned in the left portion of the septum 12 for LBB pacing. For instance, the absolute value of the minimum amplitude of negative peak 302 in waveform 301 is seen to progressively decrease in evoked response waveforms 303, 307 and 309 to a lowest absolute value of the minimum peak amplitude 322 in waveform 311, corresponding to an LBB pacing location of the pacing electrode 32. Processor 52 may track the decrease in the absolute value of the negative peak amplitude of the post-pace QRS signal as the pacing electrode is advanced and adjust a user feedback signal generated as a visual or audible representation of the pacing electrode advancement as the negative peak amplitude 302 decreases toward a minimum negative peak amplitude 322. For example, the progression of a progress bar or wheel and/or the frequency of a flashing LED and/or audible beep may be adjusted as the negative peak amplitude of the evoked QRS signal decreases to indicate that the pacing electrode is approaching the LBB pacing site. In some examples, the frequency of a user feedback flashing LED or audible beep is increased to indicate that the pacing electrode 32 is getting closer and closer to the LBB pacing site. In other examples, the frequency may be decreased to indicate to a user to advance the pacing electrode 32 more slowly, e.g., by slower rotation of a helical pacing electrode, as the LBB pacing site is approached to avoid perforation of the left border 13 of the septum 12.

Other features that may be determined by processor 52 from the V1 ECG signal 320 during pacing electrode advancement include the time interval from a delivered pacing pulse 318 to the maximum absolute peak amplitude, e.g., time intervals 305 and 326; the positive peak amplitude, e.g., amplitude 312 and 324; the peak-to-peak width between the negative minimum and positive maximum peaks, e.g., time intervals 308 and 328; the peak-to-peak amplitude difference, e.g., differences 314 and 325 shown as the positive peak amplitude minus negative peak amplitude; and the ratio of the positive peak amplitude to the negative peak amplitude of the pacing-evoked QRS signal. As observed in diagram 300, the time interval 326 from the pacing pulse 318 to the absolute maximum peak 324 (a positive peak) in evoked response waveform 311 is increased compared to the time interval 305 from the pacing pulse 318 to the absolute maximum peak (a negative peak) in evoked response waveform 301. The evoked response positive peak amplitude 324, peak-to-peak amplitude difference 325 and positive peak amplitude to negative peak amplitude ratio all increase as the pacing electrode 32 delivering the pacing pulses is advanced from right to left through the septum 12. The peak-to-peak width 328 decreases compared to peak-to-peak width 308 as the pacing electrode 32 is advanced from right to left through the septum 12. One or more of these features or changes in the general morphology waveform from a negative polarity, "W" shaped waveform 301 to the positive narrow peak waveform 311 may be determined by processor 52 during pacing electrode advancement.

A user feedback signal may be adjusted by processor 52 as one or more of these determined features change during pacing electrode advancement. In some examples, processor 52 controls the user feedback signal to be adjusted in proportion to the change detected in one or more of the determined evoked response signal features. For example, a rapid change in the positive peak amplitude to negative peak amplitude ratio (or other determined feature) is indicated to the user by a rapidly blinking LED, moving progress bar or wheel and/or beeping tone. As the user slows advancement of the tip electrode 32, the user feedback signal may be adjusted more slowly in proportion to a slower change in the positive peak amplitude to negative peak amplitude ratio or other determined ECG V1 QRS signal feature.

Figure 8:
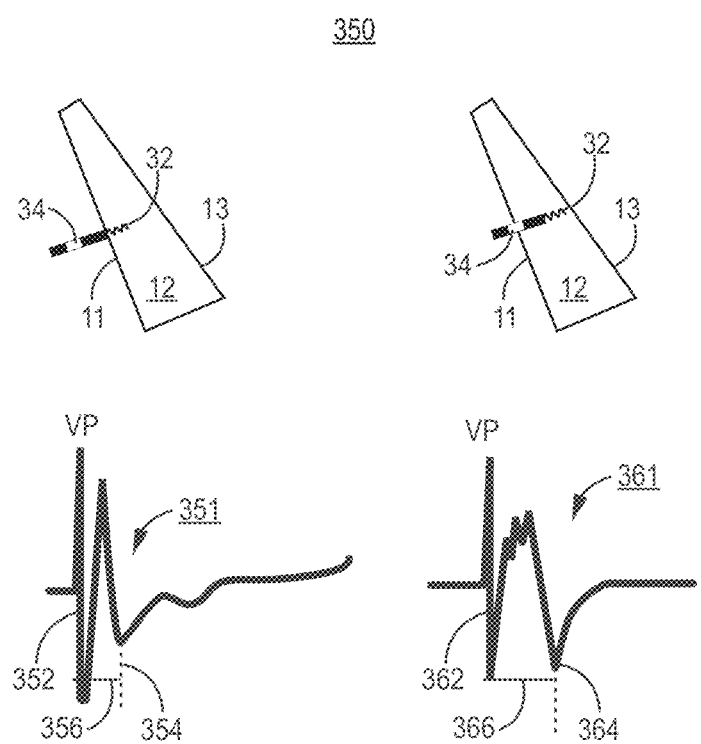
FIG. 8 is a diagram of evoked response signals included in the EGM signal of FIG. 4.

FIG. 8 is a diagram 350 of evoked response signals 351 and 361 of an EGM signal acquired using the pacing electrode 32 and a selected return anode during pacing pulse delivery via the pacing electrode 32. It is to be understood that techniques described here with reference to the lead-based pacing electrode 32 for determining an LBB signal following a pacing pulse (or during an intrinsic ventricular rhythm) may be used in conjunction with a housing-based electrode, e.g., electrode 132 of pacemaker 114, instead of a lead-based electrode. The evoked response signals 351 and 361 may be received via electrodes 32 and 34 of lead 18, for example, following delivery of a pacing pulse 352 and 362, respectively, using pacing electrode 32 as the cathode and ring electrode 34 as the anode. The EGM signal may be obtained by coupling electrical connectors to the proximal lead connector. Alternatively, a delivery tool or catheter-based return anode or a cutaneous, surface electrode may be used in conjunction with the cathode pacing electrode 32. Processor 52 may be configured to determine one or more features of the evoked response signal 351, 361 as the pacing electrode 32 is advanced from right to left through the ventricular septum 12. The overall morphology of the evoked response signals 351, 361 may be determined and compared to LBB signal morphology criteria, e.g., using a wavelet transform or other morphology waveform analysis technique. Additionally or alternatively, one or more features of the evoked response signals 351, 361 may be determined, such as a maximum peak amplitude, minimum peak amplitude, peak-to-peak amplitude, peak-to-peak width (as a time interval), pacing pulse to peak time interval, maximum positive-going slope, maximum negative-going slope, number of peaks, number of inflection points, polarity of peaks, etc. Changes in selected features of the EGM signal may be monitored by processor 52 to detect a change from evoked response signal 351 to evoked response signal 361 as the pacing electrode 32 is advanced.

To illustrate, processor 52 may be configured to detect the minimum peaks 354 and 364 of respective evoked response waveforms 351 and 361. Processor 52 may determine a time interval 356 from pacing pulse 352 to minimum negative peak 354 when the pacing electrode 32 is first advanced within a right portion of septum 12. The time interval 356 may be determined as pacing pulses are delivered while the pacing electrode 32 is advanced through septum 12. As observed in FIG. 8, the time interval 366 to minimum negative peak 364 when the pacing electrode 32 is positioned in the left portion of septum 12 is increased compared to time interval 356 when the pacing electrode 32 is in the right portion of the septum 12. When the time interval 366 is determined to be greater than a threshold time interval, processor 52 may detect the evoked response waveform 361 as an LBB signal indicative of placement of the pacing electrode at an LBB pacing site. Processor 52 may adjust a user feedback signal as increases in the time interval from the pacing pulse delivery to the minimum negative peak are detected and/or changes in another fiducial point or morphology metric of the evoked response signals 351, 361 are detected. In response to detecting the LBB signal based on morphology analysis of the EGM signal during pacing, processor 52 may generate a user feedback signal indicating LBB pacing site placement of the pacing electrode 32.

Figure 9:
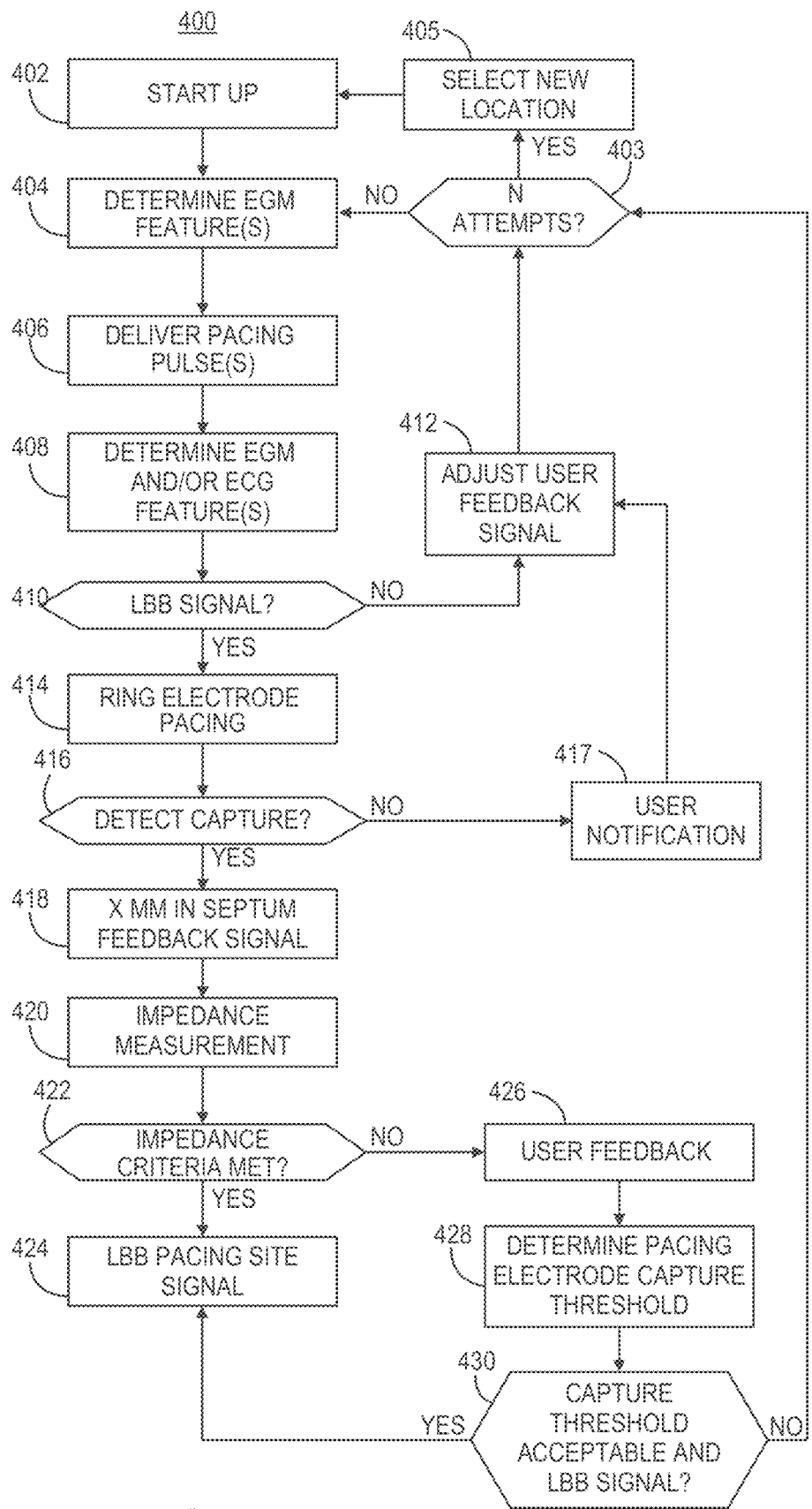
FIG. 9 is a flow chart of a method for detecting placement of a pacing electrode at an LBB pacing site according to another example.

FIG. 9 is a flow chart 400 of a method for detecting placement of a pacing electrode at an LBB pacing site according to another example. Upon starting up, at block 402, processor 52 may generate a user prompt displayed on display unit 54 instructing the user to begin advancing the pacing electrode 32. The impedance measurement unit 62 may determine the electrical impedance between the pacing electrode and a selected anode electrode and detect an increase in impedance due to the pacing electrode coming into contact with and/or entry into the right septal wall from within the RV blood pool. In other examples, processor 52 may detect an injury current in the EGM signal received via the pacing electrode indicating that the pacing electrode has entered the septum. A user notification may be generated by processor 52 that indicates that the pacing tip electrode 32 is positioned for advancement into the septum. The user notification may instruct the user to advance the tip electrode 32 by a predetermined number of rotations, e.g., 2 or more clockwise rotations of the proximal lead connector of lead 18 (FIG. 1) or the intracardiac pacemaker housing 115 (FIG. 3).

At block 404, processor 52 may determine EGM signal features during the intrinsic heart rhythm. processor 52 may determine EGM signal features during the intrinsic rhythm after a predetermined number of clockwise rotations have been performed and confirmed by a user input received via user interface 56. In other examples, processor 52 may be sensing the EGM signal and determining EGM signal features on a beat-by-beat basis, e.g., as the user is advancing the pacing electrode 32. At block 406, processor 52 may control pulse generator 60 to generate one or more pacing pulses that are delivered via the pacing electrode and a return anode electrode, e.g., a cutaneous or subcutaneous return anode electrode used during testing, a return anode that may be included on the delivery catheter or tool, or a proximal ring electrode carried by a pacing lead or intracardiac pacemaker, e.g., proximal ring electrode 34 or 134 of FIGS. 2 and 3, respectively. One or more features of the evoked response waveform are determined at block 408 from at least one ECG signal and/or the EGM signal. Any of the example features described above in conjunction with FIGS. 6-8 may be determined at block 408.

At block 410, processor 52 determines whether the determined features during the intrinsic and/or paced rhythm meet LBB signal criteria at block 410. Example criteria may include detection of the intrinsic LBB potential signal, an injury current based on elevated baseline amplitude after the LBB potential signal, the LV intrinsic activation time between the LBB potential signal and QRS maximum peak being within an LBB signal range, LV paced activation time from a pacing pulse to the evoked response peak being within an LBB signal range, and/or any of the changes described above in the ECG signals that occur in the pacing-induced evoked response as the pacing electrode 32 is advanced from the right portion to the left portion of the septum 12.

In one example, processor 52 determines that LBB signal criteria are met at block 410 when at least two out of the following five criteria are satisfied: 1) detect a post-pace V1 or V2 ECG signal that resembles RBB block, e.g., by detecting a delayed evoked response peak in V1 ECG signal compared to the V5 or V6 activation time as described above or detect a notched evoked response in the V2 ECG signal as described above; 2) detect a short post-pace LV activation time, e.g., less than 100 milliseconds or between 70 and 90 milliseconds in the V5 or V6 ECG signal; 3) detect the LBB potential signal from the EGM signal during an intrinsic ventricular rhythm; 4) detect correction of an LBB block signal waveform in a patient that has LBB block, e.g., by detecting a narrow evoked response width 256 (column 208, FIG. 6) of the post-pace evoked response in the V5 or V6 ECG signal, which may be detected as a decrease from the evoked response width 246 after initially entering the septum (column 204) and 5) detect a premature ventricular contraction (PVC) that results in a QRS waveform similar to a RBB block signal (as described above). During pacing electrode insertion, mechanical stretching of the cardiac cells can induce PVCs at the site of the pacing electrode 32. When this occurs in the left portion of the septum near the LBB, activation in the left septum due to mechanical stretching may cause a QRS waveform that appears similar to a RBB block signal since the RV is electrically activated later than the LV. Processor 52 may monitor RR intervals (time interval between two consecutively detected R-wave threshold crossings). When a short RR interval is detected that is less than a PVC interval threshold (e.g., less than 500 ms), the V1/V2 ECG signals and/or the V5/V6 ECG signals may be analyzed to determine if an RBB block signal or an LBB block signal is detected. Detection of an RBB block signal following a PVC may be used toward satisfying LBB signal detection criteria for confirming an LBB pacing site location of the pacing electrode 32. When at least two out of five of the above-listed criteria are satisfied at block 410, an LBB signal is detected by processor 52 at block 410 in some examples.

If the LBB signal criteria are not met at block 410, as determined by processor 52 based on analysis of the intrinsic EGM signal and/or pacing-induced evoked response signals of one or more ECG signals and/or the EGM signal, processor 52 may generate or adjust a user feedback signal at block 412. The user feedback signal may be an implant progress indicator generated according to the number of turns prompted to the user since start up at block 402 in some examples. For instance the total number of turns prompted to the user in user feedback signals generated by processor 52 may be counted by processor 52 (with or without user confirmation via user interface 56), and the user feedback signal may prompt the user to apply up to a maximum number of turns based on an expected ventricular septum thickness. In other examples, the user feedback signal is an implant progress indicator based on the EGM and/or ECG signal features determined at blocks 404 and/or 408. For example, the user feedback signal may be adjusted to indicate a progression that is within the right portion of the septum 12, e.g., based on detection of a characteristic "W" shaped waveform in the V1 ECG signal or an LBB block signal in the ECG signal following a pacing pulse. The user feedback signal may be adjusted to indicate a progression that is within a mid-portion of the septum 12 based on the morphology or characteristic features of the evoked response waveforms being an intermediate form of the ECG and/or EGM signals when the pacing electrode is between the right and left portions as described in conjunction with FIGS. 6 and 7.

Based on the user feedback signal generated by processor 52, the user may be prompted to advance the pacing electrode 32 further, and processor 52 may repeat the EGM and/or ECG signal analysis of blocks 404 through 410. When processor 52 determines that LBB signal criteria are met at block 410, external device 50 may execute additional tests for verifying an acceptable position of the pacing electrode 32 for LBB pacing. In one example, processor 52 may control pulse generator 54 to perform a pacing capture test by generating and delivering one or more pacing pulses via a proximal electrode, e.g., ring electrode 34 of lead 18, selected as the cathode electrode and the pacing electrode 32 or a cutaneous or subcutaneous electrode selected as the return anode. If capture is detected following a pacing pulse delivered by the proximal electrode 34, e.g., based on an evoked response signal detected within a capture window following the pacing pulse, a user feedback notification may be generated at block 418. Capture during pacing from the proximal ring electrode 34 indicates that the proximal ring electrode 34 is in contact with the septum such that at least the length of the distal portion of lead 18 extending from pacing electrode 32 to ring electrode 34 is within the septum 12. If the proximal ring electrode 34 and pacing electrode 32 are known to be 10 millimeters (mm) apart, as an example, processor 52 may generate a user notification that the pacing electrode 32 has been advanced at least 10 mm into the septum at block 418.

If capture is not detected following a pacing pulse delivered by the proximal ring electrode 34 selected as the cathode electrode, processor 52 may generate a user notification (at block 417) for display on display unit 54 that the pacing electrode 32 is less than 10 mm (as an example) within the septum. Processor 52 may adjust the user feedback signal indicating pacing electrode progression within the septum at block 412. Processor 52 may prompt the user to advance the pacing electrode 32 with caution, e.g., by slowly advancing at least one more turn. This process of EGM and/or ECG signal analysis during the intrinsic and/or paced rhythm may be repeated at blocks 404-410 to detect an LBB signal and confirm adequate advancement based on pacing capture achieved at the proximal ring electrode 34 (blocks 414 and 416). In other examples, instead of or in addition to a pacing capture test using proximal ring electrode 34, impedance measurement unit 62 may acquire an impedance signal by applying a drive signal to the proximal ring electrode 34 and recording the resulting signal using a recording pair of electrodes, which may be any available pair of electrodes and may include cutaneous or subcutaneous return electrode(s). A decrease in impedance indicating that the proximal ring electrode 34 has moved from the RV blood pool to being in contact with or into the septum 12 may be used to confirm that the pacing electrode 32 has been inserted into the septum 12 a distance that is at least equal to the interelectrode spacing.

In some examples, processor 52 may control impedance measurement unit 62 to determine pacing electrode impedance at block 420 to verify that the pacing electrode is not over-advanced into the LV chamber. The pacing electrode impedance may be determined by delivering a drive signal using pacing electrode 32 and proximal ring electrode 34 (or another return electrode) and determining the resulting impedance, which may be determined as the resulting voltage signal across the recording electrode pair when a known drive current signal is delivered. The pacing electrode impedance may be verified to be within an acceptable range at block 422. The acceptable range may be based on an impedance determined while the pacing electrode 32 is within the septum 12, e.g., before an LBB signal is detected but after verifying entry into the septum 12, e.g., based on injury current signal. The acceptable range may be greater than an impedance determined when the pacing electrode 32 remains in the RV blood pool during the start-up procedure. When the pacing electrode impedance is low, e.g., less than a threshold impedance or within a threshold range of an RV blood pool baseline impedance at block 422, the pacing electrode 32 may be over-advanced, perforating into the left ventricular blood pool. In response to detecting a low impedance corresponding to impedance in a blood pool due to over-advancement, processor 52 may generate a user feedback on display unit 54 at block 426 instructing the user to retract or reverse the rotation of the pacing electrode 32. Processor 52 may re-determine the impedance and prompt the user and/or adjust the user feedback signal accordingly until the impedance increases, indicating that the pacing electrode is within the septal tissue again.

In some examples, processor 52 may determine the pacing capture threshold at block 428. A capture threshold search may be performed by delivering pacing pulses at multiple pacing pulse amplitudes and/or pacing pulse widths until capture is lost. In other examples, capture may be verified by delivering a unipolar pacing pulse via the pacing electrode 32 (as the cathode) and a cutaneous or subcutaneous anode electrode or a catheter based anode electrode using a nominal or default pacing pulse amplitude and pulse width at block 428 to verify that capture is achieved. In some examples, the proximal ring electrode 34 (or proximal electrode 134 in the case of intracardiac pacemaker 114) may be used as the return anode in a bipolar pacing pair. For example, a unipolar or bipolar pacing pulse of 1 volt amplitude and 0.5 milliseconds (ms) may be delivered. If capture is detected, based on an evoked response signal detection following the pacing pulse, and the LBB signal criteria are still being met at block 430, processor 52 may generate a user feedback signal indicating placement of the tip electrode 32 at an LBB pacing site (block 424).

In some instances, criteria for detecting LBB pacing location of the pacing electrode 32 may not be satisfied after several attempts of advancing (and in some cases retracting) the pacing electrode 32. When LBB signal and/or capture testing criteria remain unmet after a maximum number of attempts, e.g., 3 attempts, of adjusting the pacing electrode position after entering the septum (block 403), a user feedback signal may be generated at block 405 to select a new location for the pacing electrode 32. The user may retract the pacing electrode 32 out of the septum 12 and enter the septum 12 at a new location or angle. Processor 52 may repeat determining the baseline signals and measurements made during the start-up procedure at block 402 as needed.

While analysis of ECG and/or EGM signals during intrinsic and/or pacing pulse delivery, pacing capture testing, and electrode impedance testing are shown in a particular order in FIG. 9, it is contemplated that such testing may be performed in a different order or combination than the particular order and combination shown. Furthermore, one or more of the tests or criteria shown in FIG. 9 may be omitted altogether. Although the LBB signal criteria at block 410, ring electrode capture criteria (and/or ring electrode impedance criteria) at block 414, and pacing electrode impedance criteria applied at block 422 are shown as ordered, sequential operations, it is recognized that these operations may be performed in an alternating or parallel manner. In some cases, over-advancement may occur resulting in a drop in pacing electrode impedance before the LBB signal is detected. As such, it is to be understood that the operations shown in the flow chart 400 and other flow charts presented herein may occur in a different order, repeated in an alternating manner, and/or performed in parallel or concurrently until the criteria for detecting LBB pacing site location of the pacing electrode 32 are met, which may include detecting a LBB signal during pacing and/or during an intrinsic rhythm, detecting capture by the proximal ring electrode 34, meeting an impedance requirement, and/or meeting a pacing capture threshold requirement.

Figure 10:
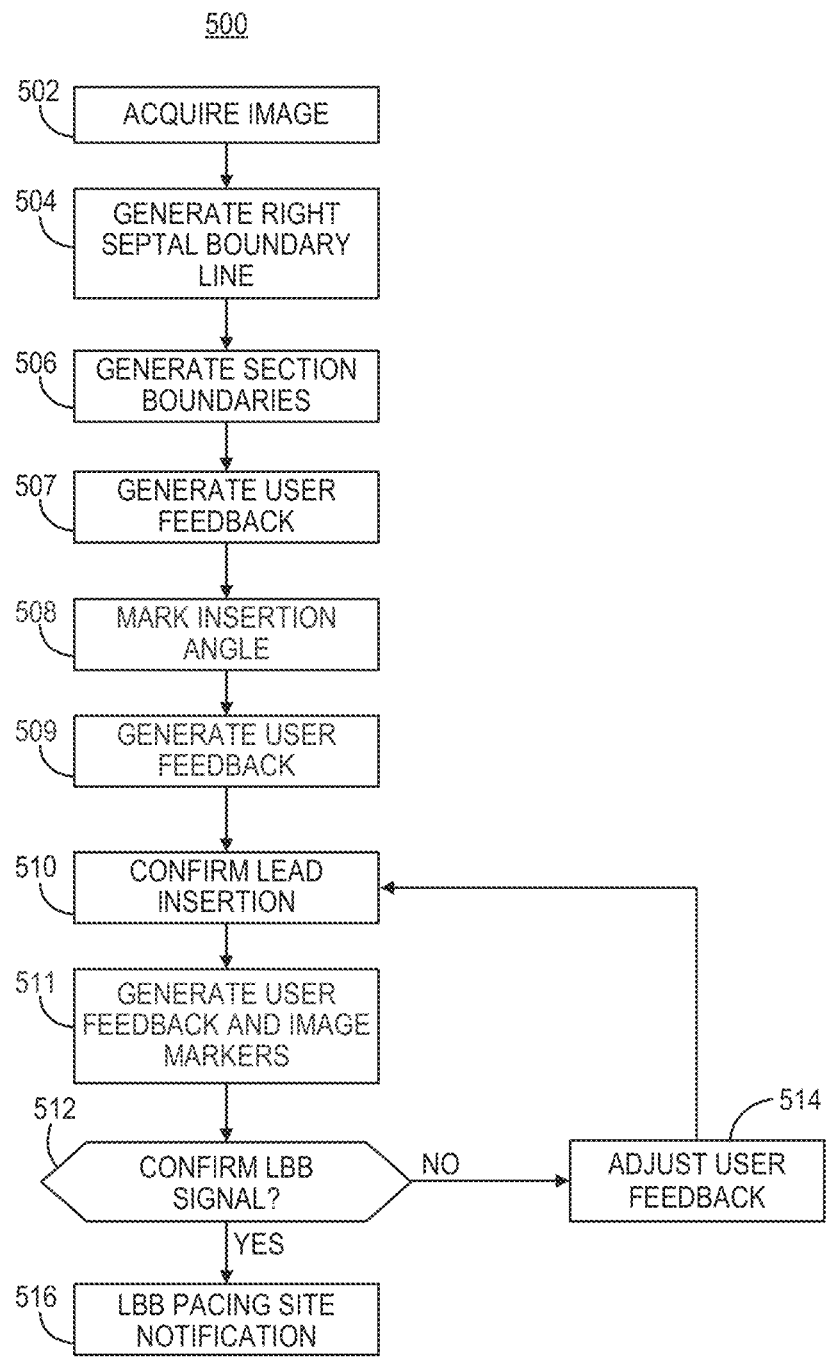
FIG. 10 is a flow chart of a method performed by the system of FIG. 1 for guiding pacing electrode implantation for LBB pacing according to another example.

FIG. 10 is a flow chart 500 of a method performed by the system of FIG. 1 for guiding pacing electrode implantation for LBB pacing according to another example. In some examples, the medical device system performing the presently disclosed techniques generates user feedback signals for guidance of pacing electrode placement based on a cardiac image generated by an imaging unit, for example imaging unit 70 shown in FIG. 1. Image-based guidance may be provided to aid the implanting clinician in advancing the pacing electrode 32/132 to an entry point along the ventricular septum, e.g., along the right ventricular septum. After the pacing electrode 32/132 is guided to the entry point along the ventricular septum, the techniques described above for determining when the pacing electrode is at an LBB pacing site within the left septum, based on cardiac signal analysis, may be used to guide the pacing electrode advancement. At block 502, the imaging unit 70 generates a cardiac image, which may be a fluoroscopy image or an echocardiography image as examples. In one example, the image is obtained by a fluoroscopy imaging unit at a right anterior oblique (RAO) 30 degree view to obtain a projection of the septum from the right.

Figure 11:
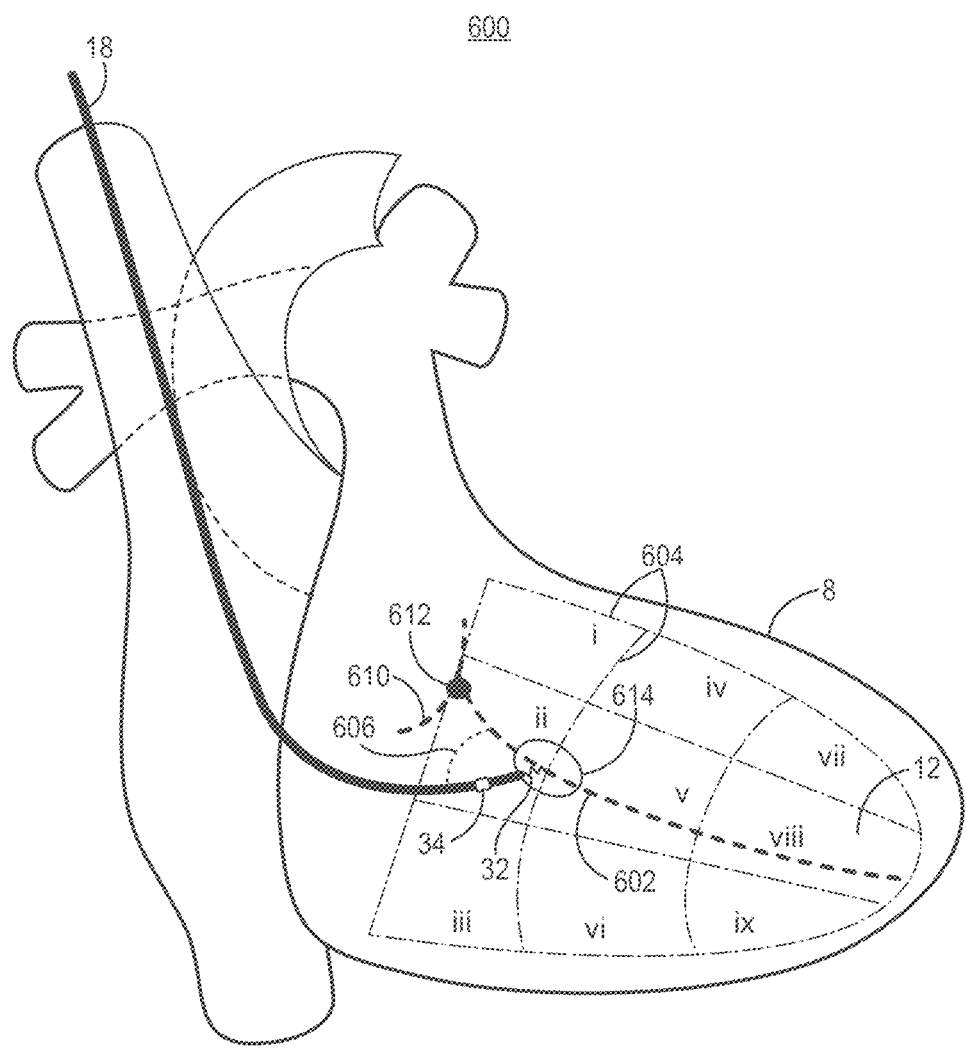
FIG. 11 is a conceptual diagram of a cardiac image including a view of the ventricular septum

FIG. 11 is a conceptual diagram 600 of a cardiac image of heart 8 taken from an RAO view of septum 12. In this example, lead 18 is advanced within a catheter (not shown) into the RV. A contrast dye may be injected via the catheter to visualize the right ventricular border of septum 12. At block 504 of FIG. 10, a boundary line 602 (shown in FIG. 11) may be generated to demarcate the boundary between the RV chamber and the septum. Boundary line 602 may be generated automatically, e.g., based on image contrast at the boundary of the RV chamber after injecting contrast dye. In other examples, a user may trace the RV/LV boundary using user interface 76, and imaging unit processor 72 and display 74 may cooperatively generate a boundary line 602 on the cardiac image in response to the user input.

At block 506 of FIG. 10, with continued reference to FIG. 11, the processor 72 may generate section lines 604 dividing the septum 12 into a predetermined number of sections or regions. In the example shown in FIG. 11, section lines 604 are generated to divide the septum 12 into nine sections labeled i through ix. The section lines 604 and section labels (e.g., i through ix) may be displayed on imaging unit display 74.

Referring again to FIG. 11, a second boundary line 610 may be generated in some examples demarcating the annulus of the tricuspid valve between the right atrium and right ventricle. The second boundary line 610 may be traced by a user or generated automatically or semi-automatically by imaging unit processor 72 based on an image recognition algorithm that differentiates the contrast between injected contrast dye in the RV and the boundary of the valve annulus. The intersection 612 of the septal boundary line 602 and the valve annulus boundary line 610 may be marked on the imaging unit display 74 to indicate an approximate location of the His bundle. In some examples, a marker of the tricuspid valve septal leaflet may be generated on cardiac image 600.

In other examples, the user may mark a location of the His bundle using user interface 76. The location of the His bundle may be identified based on observation of a His bundle potential signal appearing in the EGM signal generated by external device display unit 54 as the pacing electrode 32 is advanced into the RV. The boundary line 602 may be generated by imaging unit processor 72 extending from the identified location of the His bundle 612 to the RV apex in some examples. A section line 604 that separates the upper middle section ii and the middle section v may be drawn approximately 10 to 20 millimeters below intersection 612. A target pacing electrode entry region boundary 614 may be generated on imaging unit display 74 along septal boundary line 602, approximately 10 to 20 millimeters below intersection 612, e.g., centered on the intersection of septal boundary line 602 and the section line 604 between sections ii and v. This target entry region boundary 614 indicates to the user the region to position pacing electrode 32/132 against the septum 12 for advancement into septum 12 for delivering pacing along the distal His including the LBB or along the LBB.

At block 507, imaging unit processor 72 (or external device processor 52) may generate a user feedback signal at block 507 prompting the user to advance pacing electrode 32 to a location against the septum 12 in the target region 614, in a location that is near the boundary between sections ii and v (according to the example labeling shown), or generally about 10-20 millimeters below intersection 612 for LBB pacing placement. Once positioned against septum 12, the generated image 600 may be used to confirm that the pacing lead 18 (or housing 115 of pacemaker 114) is perpendicular to the septum 12, e.g., at an angle 606 that is between 70 and 90 degrees to septum 12. This angle 606 may be confirmed using the RAO 30 degree view or a left anterior oblique (LAO) view. An insertion angle 606 may be marked at block 508 and the angle may be measured by imaging unit processor 72. If the angle 606 is less than a threshold angle, e.g., 70 degrees, user feedback is generated at block 509 to prompt the user to adjust the angle. If the angle 606 is approximately 70 to 90 degrees, the user feedback generated at block 509 may prompt the user to advance the pacing electrode 32/132 into septum 12. The user may be prompted to advance the pacing electrode 32/132 by rotating the electrode a predetermined number of rotations.

After advancement, confirmation that the pacing electrode 32/132 is inserted in the septum 12 may be performed at block 510 by external device 50. Confirmation may be performed by injecting contrast dye to verify that pacing electrode 32 is within the left portion of septum 12. After contrast dye is injected in the RV, the cardiac image may enable visual determination that the proximal ring electrode 34 is in or at the septal wall 12 to verify that the pacing electrode 32 is at least a corresponding inter-electrode distance into the septum. The imaging unit processor 72 may detect the ring electrode location relative to the septal wall boundary line 602 based on image analysis by detecting a radio-opaque contrast marker carried by the ring electrode 34 or by the pacing lead body at the location of the ring electrode 34. When the ring electrode marker is detected to be past the septal boundary line 602, a user feedback signal may be generated confirming insertion of the pacing electrode 32 at least the inter-electrode spacing into septum 12.

In some examples, the distance from the septal boundary line 602 to the radio-opaque marker representing the location of proximal ring electrode 34 may be estimated and added to the inter-electrode distance to estimate a total distance from the right septal border to the pacing electrode 32, which may be reported to the user via imaging unit display 74 or external device display unit 54.

In other examples, confirmation of lead insertion at block 510 may include determining the pacing electrode impedance (a very low impedance may indicate that the pacing electrode is still in the RV blood pool or that perforation of pacing electrode 32 into the LV blood pool has occurred), determining the pacing capture threshold using the pacing electrode 32 as the cathode, determining if pacing pulse delivery via the proximal ring electrode 34 as the cathode achieves capture, and/or detecting injury potential from the EGM signal.

When over-advancement of the pacing tip electrode 32 is detected, e.g., based on cardiac electrical signals, impedance measurements, and/or contrast dye injection, the processor 72 of imaging unit 70 may generate a marker or icon on display unit 74 at block 511 indicating the pacing electrode location in the cardiac image displayed on image display unit 74. This marker provides a landmark to the user indicating a location that is over-advancement, beyond the left border of the septum 12. The imaging unit 70 may be configured to generate a snapshot image of the location of pacing lead 18 relative to the cardiac image and any generated boundary lines, segment lines and other markers. The snapshot may be stored in imaging unit memory 74 for a visual comparison by the user if the user decides to withdraw the pacing electrode 32 to reposition in a new location when LBB signal criteria are not met.

In some examples, after using image guided placement of lead 18, processor 52 of external device 50 may analyze the EGM and/or one or more ECG signals during the intrinsic heart rhythm and/or during pacing as described above for detecting an LBB signal at block 512, e.g., according to any of the techniques described above. If an LBB signal is not confirmed at block 512, processor 52 may adjust a user feedback signal 514 to prompt the user to further advance the pacing electrode 32/132 until the LBB signal is confirmed at block 512. At block 516, the external device processor 52 may generate a notification displayed on display unit 54 indicating that the pacing electrode 32/132 is positioned for LBB pacing. When an LBB signal is detected during advancement of the pacing electrode 32/132, the imaging unit 70 may generate a marker at one or more locations indicating sites corresponding to LBB signal detection in response to a signal received from external device 50 at block 512. In this way, the user may adjust the pacing electrode position to a location corresponding to LBB signal detection as needed, e.g., after over-advancement is detected and retraction of the pacing electrode is needed or when an unacceptable LBB pacing capture test result occurs.

Figure 12:
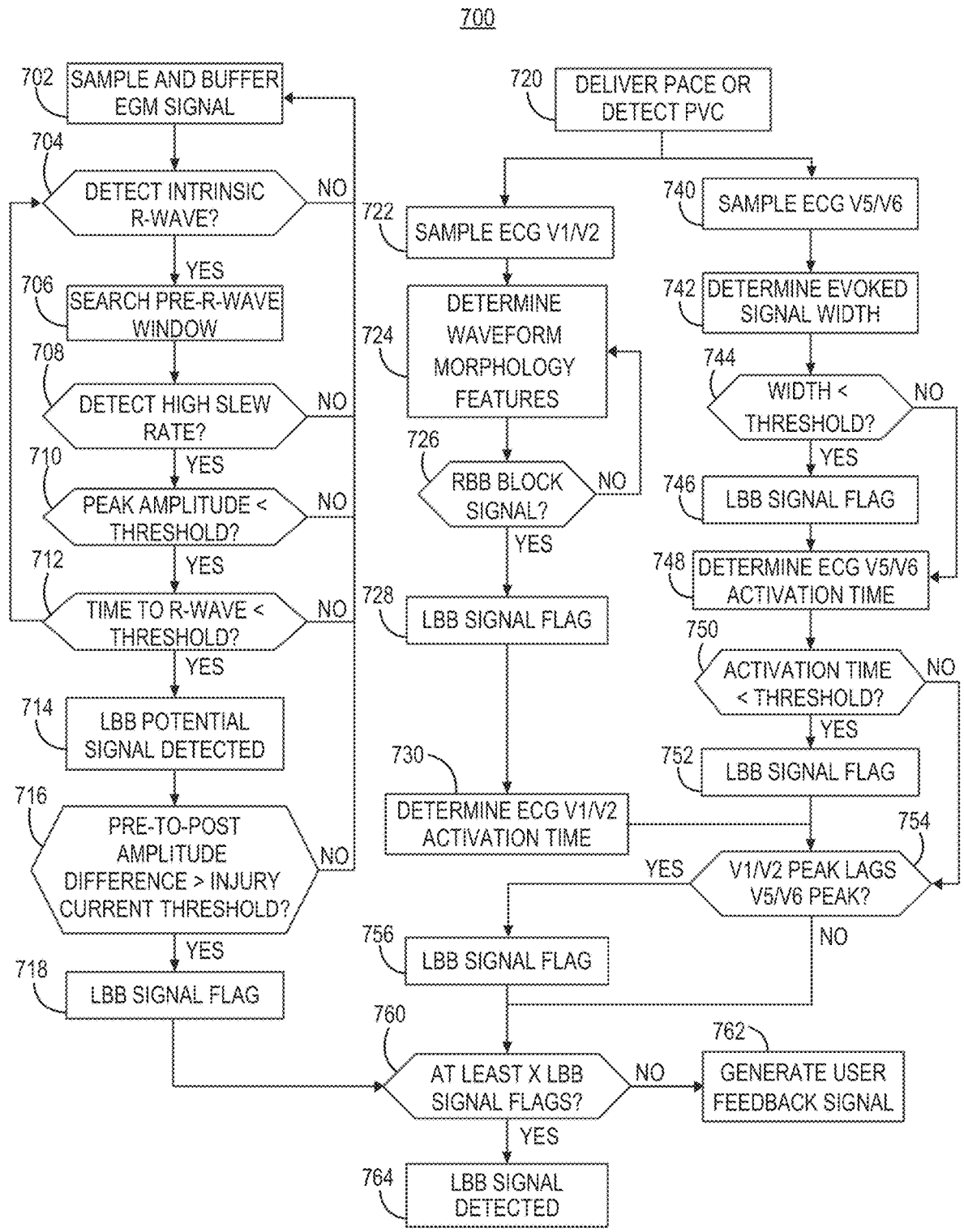
FIG. 12 is a flow chart of a method performed by a medical device system for detecting an LBB signal according to one example.

FIG. 12 is a flow chart 700 of a method performed by external device processor 52 for detecting an LBB signal according to one example. As described above, an LBB signal may be detected based on one or any combination of the detection of an intrinsic LBB potential signal in the pacing electrode EGM signal, injury current detection, detection of a RBB block signal in a V1 or V2 ECG signal following a pacing pulse or a detected PVC, a wide evoked response signal in the V5 or V6 ECG signal, an early LV activation time in the V5 or V6 ECG signal, and/or detection of a correction of LBB block signal as the pacing electrode is advanced. The process of flow chart 700 is described with reference to the lead-based pacing electrode 32 for the sake of convenience. It is to be understood that the process of flow chart 700 may be performed in conjunction with the advancement of pacemaker 114 and housing-based pacing electrode 132.

At block 702, the external device processor 52 may sample and buffer the EGM signal sensed using the pacing electrode 32 (and any selected anode electrode) as it is advanced through the septum using any available return anode electrode. The EGM signal may be sampled at a relatively high sampling rate, e.g., 1000 Hz to enable detection of the high frequency LBB potential signal. The sampled EGM signal is buffered in external device memory 53 over a sampling window that may be up to 50 ms, as an example. At block 704, external device processor 52 detects an intrinsic R-wave from the EGM signal, e.g., in response to detecting an R-wave sensing threshold crossing by the EGM signal during a ventricular non-paced rhythm.

Upon R-wave detection, processor 52 may analyze the buffered signal over an LBB potential window at block 706, e.g., extending 10 to 40 ms earlier than the sensed R-wave, or encompassing an entirety of the sampling window. In some examples, the sampled signal may be filtered by a high pass filter to reduce or remove low frequency content from the sampled EGM signal to facilitate detection of the high frequency LBB potential signal. Processor 52 may determine a maximum slew rate, slope or peak derivative of the EGM signal during the LBB potential window prior to the R-wave detection and compare the maximum to an LBB potential signal threshold at block 708 for detecting a slew rate or slope that corresponds to an LBB potential signal. If a high slew rate or slope is not detected, an LBB potential signal is not detected, and processor 52 continues to sample and buffer the EGM signal.

When a high slew rate is detected at block 708, processor 52 may determine the maximum peak amplitude during the LBB potential window (set to exclude the QRS signal) and compare the maximum peak amplitude to a maximum LBB potential signal amplitude threshold. The LBB potential signal is a high frequency, low amplitude signal as observed in FIG. 6. If the maximum peak amplitude detected during the LBB potential signal window preceding an intrinsic R-wave is greater than the LBB potential signal threshold amplitude, processor 52 does not detect the LBB potential signal and returns to block 702.

In response to detecting a high slew rate signal with a peak amplitude less than the LBB potential signal, processor 52 may detect the LBB potential signal at block 714. In some examples, processor 52 may verify that the time from the maximum slew rate or the LBB potential signal peak amplitude to the sensed intrinsic R-wave is within an LBB potential threshold interval at block 712. When any one, two or all three of these criteria at block 708, 710 and/or 712 are satisfied, processor 52 may detect the LBB potential signal at block 714 as evidence that the pacing electrode 32 is in the left portion of the septum, proximate the LBB. In response to detecting the LBB potential signal, processor 52 may generate an LBB signal flag at block 718 indicating that at least one condition in the EGM signal during an intrinsic ventricular rhythm supports LBB signal detection.

In some examples, processor 52 may additionally verify that an injury current is detected at block 716. When the difference between the EGM signal amplitude post-potential signal and pre-potential signal is greater than a threshold, as determined at block 716, processor 52 may set the LBB signal flag at block 718. As described above in conjunction with FIG. 6, an injury current may be detected in conjunction with the LBB potential signal when the pacing electrode 32 is advanced into the left septum.

At block 720, processor 52 may control pulse generator 60 to deliver a pacing pulse using the pacing electrode 32, or processor 52 may detect a PVC as the pacing electrode 32 is pushed into the left septum. A PVC may be detected by processor 52 by determining a time interval from a pacing pulse or intrinsic R-wave to a consecutively sensed intrinsic R-wave and determining the time interval to be less than a PVC threshold interval. When a pacing pulse is delivered or a PVC is detected, processor 52 may sample the V1 and/or V2 ECG signal at block 722 to determine QRS features at block 724. Features may include an overall waveform morphology, maximum and minimum peak amplitudes and/or slopes and patterns thereof, or other features that enable processor 52 to detect a notched V1 or V2 ECG signal waveform that resembles an RBB block QRS morphology. When a notched waveform, e.g., as shown by the V2 signal in column 208 of FIG. 6 is detected, processor 52 may generate an LBB signal flag at block 728 as evidence that the pacing electrode 32 is within the left portion of the septum. In some examples, the morphology feature determination and analysis performed at blocks 724 and 726 may be performed to detect a "W" shaped waveform in the V1 ECG signal following a pacing pulse or PVC. When a "W" shaped morphology is detected as evidence of the pacing electrode 32 remaining within the right portion of the septum (e.g., see ECG V1 signal in column 204, FIG. 6), processor 52 does not generate an LBB signal flag. When a "W" shaped morphology is not detected, processor 52 may generate the LBB signal flag at block 728. Any feature or combination of features of the V1 and/or V2 ECG signals that are characteristic of RBB block signal morphology may be determined and compared to LBB signal criteria at block 726 for detecting evidence of placement of the pacing electrode 32 in the left septum in proximity to the LBB.

At block 740, processor 52 samples the V5 and/or V6 ECG signal following a pacing pulse or detected PVC. At block 742, processor 52 may determine the signal width of an evoked response signal following a pacing pulse delivered by pacing electrode 32. When the evoked response signal width is less than an LBB signal threshold width, as determined at block 744, processor 52 may generate an LBB signal flag at block 746. The LBB signal threshold width may be defined based on the evoked response signal width determined when the pacing electrode 32 is first advanced into the right portion of the septum. In this way, a relative decrease in the evoked response signal width may be detected. Similarly, other LBB signal criteria referred to herein as being used by processor 52 in detecting an LBB signal may be based on an initial evoked response signal feature that is determined when the pacing electrode 32 is first advanced into the right portion of the septum 12 such that a relative change in the evoked response signal corresponding to a change in position from the right portion of the septum to the left portion in the septum is detected by processor 52.

Processor 52 may additionally or alternatively determine an activation time as the time interval from a delivered pacing pulse to the maximum peak of the evoked response signal in the V5 and/or V6 signal (e.g., see activation time 254 in the V6 ECG signal of column 208, FIG. 6). The activation time may be compared to an activation time threshold at block 750. When a short activation time is detected, e.g., 70 to 90 ms, in the V5 or V6 ECG signal following a pacing pulse, processor 52 may generate an LBB signal flag at block 752.

Processor 52 may determine the activation time in the V1 and/or V2 ECG signal at block 730 and compare the V1/V2 activation time to the V5/V6 activation time at block 754. As discussed in conjunction with FIG. 6 above, a relatively longer activation time in the V1/V2 signal compared to the V5/V6 signal is evidence of LBB capture since LV activation occurs quickly and the RV activation is delayed. In response to the V1/V2 signal peak lagging the V5/V6 signal peak, indicating a longer RV activation time than the LV activation time, processor 52 may set an LBB signal flag at block 756.

At block 760, processor 52 determines when at least a threshold number, e.g., at least two or at least three, LBB signal flags have been generated. When less than a threshold number, X, of LBB signal flags have been generated, processor 52 may generate a user feedback signal 762 to proceed with advancing the pacing electrode 32. All or portions of the process of flow chart 700 may be repeated as the pacing electrode 32 is advanced or after each predetermined number of turns of pacing electrode 32. When the threshold number of LBB signal flags are generated, processor 52 detects an LBB signal at block 764, indicating placement of the pacing electrode 32 for LBB pacing. A user feedback signal may be generated at block 170 (of FIG. 5) indicating that LBB pacing placement is achieved, or processor 52 may perform additional confirmation analysis, e.g., by checking the pacing electrode impedance and/or a performing a pacing capture threshold test, e.g., as described in conjunction with FIG. 5 and FIG. 9 above.

It should be understood that, depending on the example, certain acts or events of any of the methods described herein can be performed in a different sequence, in parallel, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single processor, circuit or unit for purposes of clarity, it should be understood that the techniques of this disclosure may be performed by a combination of processors, units or circuits associated with, for example, a medical device system.

In one or more examples, the functions described may be implemented in hardware, software, firmware, or any combination thereof. If implemented in software, the functions may be stored as one or more instructions or code on a computer-readable medium and executed by one or more hardware-based processing units. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device system comprising:
a processor configured to:
receive imaging data corresponding to a cardiac image comprising a ventricular septum;
generate from the imaging data a boundary line corresponding to a cardiac landmark by generating a septal boundary line demarcating a boundary between a right ventricular chamber and the ventricular septum;
generate a conduction system pacing site marker based on the boundary line and the imaging data corresponding to the cardiac image, the conduction system pacing site marker intersecting with the septal boundary line and representing a target entry region along the ventricular septum for a pacing electrode being advanced to a His bundle or bundle branch pacing site;
a memory configured to store the imaging data with the boundary line and the conduction system pacing site marker for display by a display unit; and
the display unit configured to display an image superimposed by the septal boundary line and the conduction system pacing site marker, the conduction system pacing site marker intersecting with the septal boundary line.

2. The medical device system of claim 1, wherein the processor is configured to:
generate a user feedback signal based on the conduction system pacing site marker to prompt advancement of the pacing electrode into the target entry region represented by the conduction system pacing site marker.

3. The medical device system of claim 1, wherein the processor is configured to
generate the conduction system pacing site marker by:
generating a plurality of section lines superimposed on the image that divide the ventricular septum into a plurality of sections; and
generating the conduction system pacing site marker representing the target entry region based on least one of the plurality of section lines and the septal boundary line.

4. The medical device system of claim 3, wherein the processor is configured to generate the conduction system pacing site marker by:
generating one of the plurality of section lines to divide the ventricular septum into an upper section and a middle section; and
generating the conduction system pacing site marker at an intersection of the septal boundary line and the one of the plurality of section lines dividing the ventricular septum into the upper section and the middle section.

5. The medical device system of claim 3, wherein the processor is configured to generate the conduction system pacing site marker by:
generating the plurality of section lines to divide the ventricular septum into at least nine sections comprising an upper middle section and a middle section;
generating the conduction system pacing site marker representing the target entry region along the septal boundary line and including a portion of at least one of the upper middle section and the middle section.

6. The medical device system of claim 1, wherein:
the processor is further configured to generate from the imaging data a tricuspid valve boundary line representing a location of one of an annulus or a leaflet of a tricuspid valve; and
the display unit is further configured to display the image superimposed by the tricuspid valve boundary line.

7. The medical device of claim 6, wherein:
the processor is configured to:
generate the septal boundary line intersecting with the tricuspid valve boundary line; and
generate the conduction system pacing site marker at a location inferior to the intersection of the tricuspid valve boundary line and the septal boundary line; and
the display unit is further configured to display the image superimposed by the tricuspid valve boundary line intersecting with the septal boundary line.

8. The medical device system of claim 7, wherein the processor is configured to generate the conduction system pacing site marker at a location relative to the intersection of the tricuspid valve boundary line and the septal boundary line corresponding to a location 10 millimeters to 20 millimeters inferior to the annulus of the tricuspid valve.

9. The medical device system of claim 1, wherein the processor is configured to:
determine from the imaging data corresponding to the cardiac image an angle of an elongated body associated with the pacing electrode with respect to the ventricular septum;
determine that the angle is within a threshold range; and
generate a user feedback signal to advance the pacing electrode in response to the angle being within the threshold range.

10. The medical device system of claim 9, wherein the processor is configured to determine that the angle is within the threshold range by determining that the angle is at least seventy degrees and not greater than ninety degrees.

11. The medical device system of claim 1, wherein the processor is further configured to:
determine from the imaging data corresponding to the cardiac image an angle of an elongated body associated with the pacing electrode with respect to the ventricular septum;
determine that the angle is outside a threshold range; and
generate a user feedback signal to adjust a position of the pacing electrode in response to the angle being outside the threshold range.

12. The medical device system of claim 1, wherein the processor is further configured to:
detect from the imaging data corresponding to the cardiac image a position of a proximal electrode advanced at least to a right border of the ventricular septum, the proximal electrode being proximate the pacing electrode at an interelectrode distance along an elongated body; and
generate a user feedback signal indicating that the pacing electrode is advanced at least the interelectrode distance into the ventricular septum in response to detecting the position of the proximal electrode.

13. The medical device system of claim 1, wherein the processor is configured to receive the imaging data corresponding to one of:
a fluoroscopy image; and
an echocardiography image.

14. The medical device system of claim 1, wherein the processor is further configured to:
receive a cardiac electrical signal;
determine at least one feature of the cardiac electrical signal;
compare the feature to left bundle branch signal criteria; and
detect a left bundle branch signal in response to at least the feature meeting the left bundle branch signal criteria; and
generate a user feedback signal indicating advancement of the pacing electrode into a left portion of the ventricular septum in response to the processor detecting the left bundle branch signal.

15. A method comprising:
receiving imaging data corresponding to a cardiac image comprising a ventricular septum;
generating from the imaging data a boundary line corresponding to a cardiac landmark by generating a septal boundary line demarcating a boundary between a right ventricular chamber and the ventricular septum;
generating a conduction system pacing site marker based on the boundary line and the imaging data, the conduction system pacing site marker intersecting with the septal boundary line and representing a target entry region along the ventricular septum for a pacing electrode that is to be advanced to a His bundle or bundle branch pacing site; and
storing the imaging data with the boundary line and the conduction system pacing site marker for display by a display unit; and
displaying an image superimposed by at least the septal boundary line and the conduction system pacing site marker.

16. The method of claim 15 further comprising:
generating a user feedback signal based on the conduction system pacing site marker to prompt advancement of the pacing electrode into the target entry region represented by the conduction system pacing site marker.

17. The method of claim 15, wherein generating the conduction system pacing site marker comprises:
generating a plurality of section lines that divide the ventricular septum into a plurality of sections; and
generating the conduction system pacing site marker representing the target entry region based on at least one of the plurality of section lines and the septal boundary line.

18. The method of claim 17, wherein generating the conduction system pacing site marker comprises:
generating one of the plurality of section lines to divide the ventricular septum into an upper section and a middle section; and
generating the conduction system pacing site marker at an intersection of the septal boundary line and the one of the plurality of section lines dividing the ventricular septum into the upper section and the middle section.

19. The method of claim 17, wherein generating the conduction system pacing site marker comprises:
generating the plurality of section lines to divide the ventricular septum into at least nine sections comprising an upper middle section and a middle section; and
generating the conduction system pacing site marker representing the target entry region along the septal boundary line and including a portion of at least one of the upper middle section and the middle section.

20. The method of claim 15, further comprising:
generating a tricuspid valve boundary line representing a location of one of a tricuspid valve annulus or a tricuspid valve leaflet; and
displaying the image superimposed by the tricuspid valve boundary line.

21. The method of claim 20, comprising:
generating the septal boundary line intersecting with the tricuspid valve boundary line; and
generating the conduction system pacing site marker at a location inferior to the intersection of the tricuspid valve boundary line and the septal boundary line; and
displaying the image superimposed by the tricuspid valve boundary line intersecting with the septal boundary line.

22. The method of claim 21, wherein generating the conduction system pacing site marker comprises generating the conduction system pacing site marker at a location relative to the intersection of the tricuspid valve boundary line and the septal boundary line corresponding to a location 10 millimeters to 20 millimeters inferior to the annulus of the tricuspid valve.

23. The method of claim 15, comprising:
determining from the imaging data corresponding to the cardiac image an angle of an elongated body associated with the pacing electrode with respect to the ventricular septum;
determining that the angle is within a threshold range; and
generating a user feedback signal to advance the pacing electrode in response to the angle being within the threshold range.

24. The method of claim 23, wherein determining that the angle is within the threshold range comprises determining that the angle is at least seventy degrees and not greater than ninety degrees.

25. The method of claim 15, further comprising:
determining from the imaging data corresponding to the cardiac image an angle of an elongated body associated with the pacing electrode with respect to the ventricular septum;
determining that the angle is outside the threshold range; and
generating a user feedback signal to adjust a position of the pacing electrode in response to the angle being outside the threshold range.

26. The method of claim 15, comprising:
detecting from the imaging data corresponding to the cardiac image a position of a proximal electrode advanced at least to a right border of the ventricular septum, the proximal electrode being proximate the pacing electrode at an interelectrode distance along an elongated body; and
generating a user feedback signal indicating that the pacing electrode is advanced at least the interelectrode distance into the ventricular septum in response to detecting the position of the proximal electrode.

27. The method of claim 15, wherein receiving the imaging data comprises receiving the imaging data corresponding to one of:
a fluoroscopy image; and
an echocardiography image.

28. The method of claim 15, further comprising:
receiving a cardiac electrical signal;

determining at least one feature of the cardiac electrical signal;

comparing the feature to left bundle branch signal criteria;

detecting a left bundle branch signal in response to at least the feature meeting the left bundle branch signal criteria; and generating a user feedback signal indicating advancement of the pacing electrode into a left portion of a ventricular septum in response to the processor detecting the left bundle branch signal.

29. A non-transitory computer readable medium storing instructions which, when executed by a processor of a medical device system, cause the system to:

receive imaging data corresponding to a cardiac image comprising a ventricular septum;

generate from the imaging data a boundary line corresponding to a cardiac landmark by generating a septal boundary line demarcating a boundary between a right ventricular chamber and the ventricular septum; and generate a conduction system pacing site marker based on the boundary line and the imaging data, the conduction system pacing site marker intersecting with the septal boundary line and representing a target entry region along the ventricular septum for a pacing electrode that is to be advanced to a His bundle or bundle branch pacing site;

store the imaging data with the boundary line and the conduction system pacing site marker for display by a display unit; and display an image superimposed by at least the septal boundary line and the conduction system pacing site marker.

* * * * *